(12) United States Patent
Ghosh

(10) Patent No.: US 10,449,365 B2
(45) Date of Patent: Oct. 22, 2019

(54) DETERMINING ONSETS AND OFFSETS OF CARDIAC DEPOLARIZATION AND REPOLARIZATION WAVES

(71) Applicant: Medtronic, Inc., Minneapolis, MN (US)

(72) Inventor: Subham Ghosh, Blaine, MN (US)

(73) Assignee: Medtronic, Inc., Minneapolis, MN (US)

( * ) Notice: Subject to any disclaimer, the term of this patent is extended or adjusted under 35 U.S.C. 154(b) by 189 days.

(21) Appl. No.: 15/368,199

(22) Filed: Dec. 2, 2016

(65) Prior Publication Data

US 2017/0143976 A1     May 25, 2017

Related U.S. Application Data

(63) Continuation of application No. 14/853,640, filed on Sep. 14, 2015, now abandoned, which is a
(Continued)

(51) Int. Cl.
*A61B 5/00*     (2006.01)
*A61B 5/04*     (2006.01)
(Continued)

(52) U.S. Cl.
CPC ........ *A61N 1/36507* (2013.01); *A61B 5/0402* (2013.01); *A61B 5/04017* (2013.01);
(Continued)

(58) Field of Classification Search
CPC . A61B 5/04017; A61B 5/0402; A61B 5/0452; A61B 5/1107
See application file for complete search history.

(56) References Cited

U.S. PATENT DOCUMENTS

| 4,374,382 | A | 2/1983 | Markowitz |
| 4,704,681 | A | 11/1987 | Shimizu et al. |

(Continued)

FOREIGN PATENT DOCUMENTS

| CN | 1194132 A | 9/1998 |
| CN | 101500645 A | 8/2009 |

(Continued)

OTHER PUBLICATIONS

"A Comparison of the Noise Sensitivity of Nine QRS Detection Algorithms", by Gary M. Friesen et al., IEEE Transactions on Biomedical Engineering, vol. 37, No. 1, Jan. 1990, pp. 85-98.
(Continued)

*Primary Examiner* — Paula J Stice

(57) ABSTRACT

An exemplary computer-implemented method is disclosed for detection of onset of depolarization on far-field electrograms (EGMs) or electrocardiogram (ECG)-or ECG-like signals. The method includes determining a baseline rhythm using a plurality of body-surface electrodes. The baseline rhythm includes an atrial marker and a ventricular marker. A pre-specified window is defined as being between the atrial marker and the ventricular marker. A low pass filter is applied to a signal within the window. A rectified slope of the signal within the window is determined. A determination is made as to whether a time point (t1) is present such that the rectified slope exceeds 10% of a maximum value of the rectified slope. A point of onset of a depolarization complex in the signal is determined. The point of onset occurs at a largest curvature in the signal within the window.

18 Claims, 15 Drawing Sheets

Related U.S. Application Data continuation of application No. 13/952,076, filed on Jul. 26, 2013, now Pat. No. 9,132,274.

(51) Int. Cl.
  *A61N 1/365* (2006.01)
  *A61B 5/0402* (2006.01)
  *A61B 5/0452* (2006.01)
  *A61N 1/362* (2006.01)
  *A61N 1/368* (2006.01)
  *A61B 5/0408* (2006.01)
  *A61B 5/11* (2006.01)

(52) U.S. Cl.
  CPC ........ *A61B 5/0452* (2013.01); *A61B 5/04085* (2013.01); *A61B 5/1107* (2013.01); *A61B 5/4836* (2013.01); *A61N 1/3627* (2013.01); *A61N 1/3684* (2013.01); *A61B 2562/043* (2013.01); *A61B 2562/046* (2013.01)

(56) References Cited

U.S. PATENT DOCUMENTS

| | | | |
|---|---|---|---|
| 5,048,535 | A | 9/1991 | Mitsuya |
| 5,117,824 | A | 6/1992 | Keimel et al. |
| 5,545,186 | A | 8/1996 | Olson et al. |
| 5,697,378 | A | 12/1997 | Fawaz et al. |
| 5,755,736 | A | 5/1998 | Gillberg |
| 5,903,664 | A | 5/1999 | Hartley et al. |
| 6,684,100 | B1 | 1/2004 | Sweeney et al. |
| 7,587,074 | B2 | 9/2009 | Zarkh et al. |
| 7,706,879 | B2 | 4/2010 | Burnes et al. |
| 7,894,898 | B2 | 2/2011 | Sheldon et al. |
| 8,260,406 | B2 | 9/2012 | Hardahl et al. |
| 9,132,274 | B2 | 9/2015 | Ghosh |
| 2007/0203419 | A1 | 8/2007 | Sweeney et al. |
| 2007/0293899 | A1 | 12/2007 | Sheldon et al. |
| 2009/0076403 | A1 | 3/2009 | Hopenfeld |
| 2009/0076404 | A1 | 3/2009 | Hopenfeld |
| 2009/0112108 | A1 | 4/2009 | Nelson et al. |
| 2009/0234412 | A1 | 9/2009 | Sambelashvili |
| 2010/0069767 | A1 | 3/2010 | Hardahl et al. |
| 2010/0268059 | A1 | 10/2010 | Ryu et al. |
| 2011/0004264 | A1 | 1/2011 | Siejko et al. |
| 2012/0284003 | A1 | 11/2012 | Gosh et al. |

FOREIGN PATENT DOCUMENTS

| | | |
|---|---|---|
| WO | 2009/114320 A2 | 9/2009 |
| WO | 2009114320 A2 | 9/2009 |
| WO | 2012151389 A1 | 8/2012 |
| WO | 2012/151389 A1 | 11/2012 |

OTHER PUBLICATIONS

C00001948.WOU2 (PCT/US2014/048070) PCT Notification of Transmittal of the International Search Report and the Written Opinion of the International Searching Authority.
"Detection of Multilead ECG Character Points and Assessment Based on a Reference Database", by Wenyu Ye et al., Proceedings of the 2005 IEEE, Engineering in Medicine and Biology 27th Annual Conference, Shanghai, China, Sep. 1-4, 2005, pp. 3895-3898.
Friesen et al., Gary M., "A Comparison of the Noise Sensitivity of Nine QRS Detection Algorithms", IEEE Transactions on Biomedical Engineering, vol. 37, No. 1, Jan. 1990, pp. 85-98.
Ye, Wenyu et al., "Detection of Multilead ECG Character Points and Assessment Based on a Reference Database", Proceedings of the 2005 IEEE, Engineering in Medicine and Biology 27th Annual Conference, Shanghai, China, Sep. 1-4, 2005, pp. 3895-3898.
(PCT/US2014/048070) PCT Notification of Transmittal of the International Search Report and the Written Opinion of the International Searching Authority, dated Oct. 23, 2014, 12 pages.

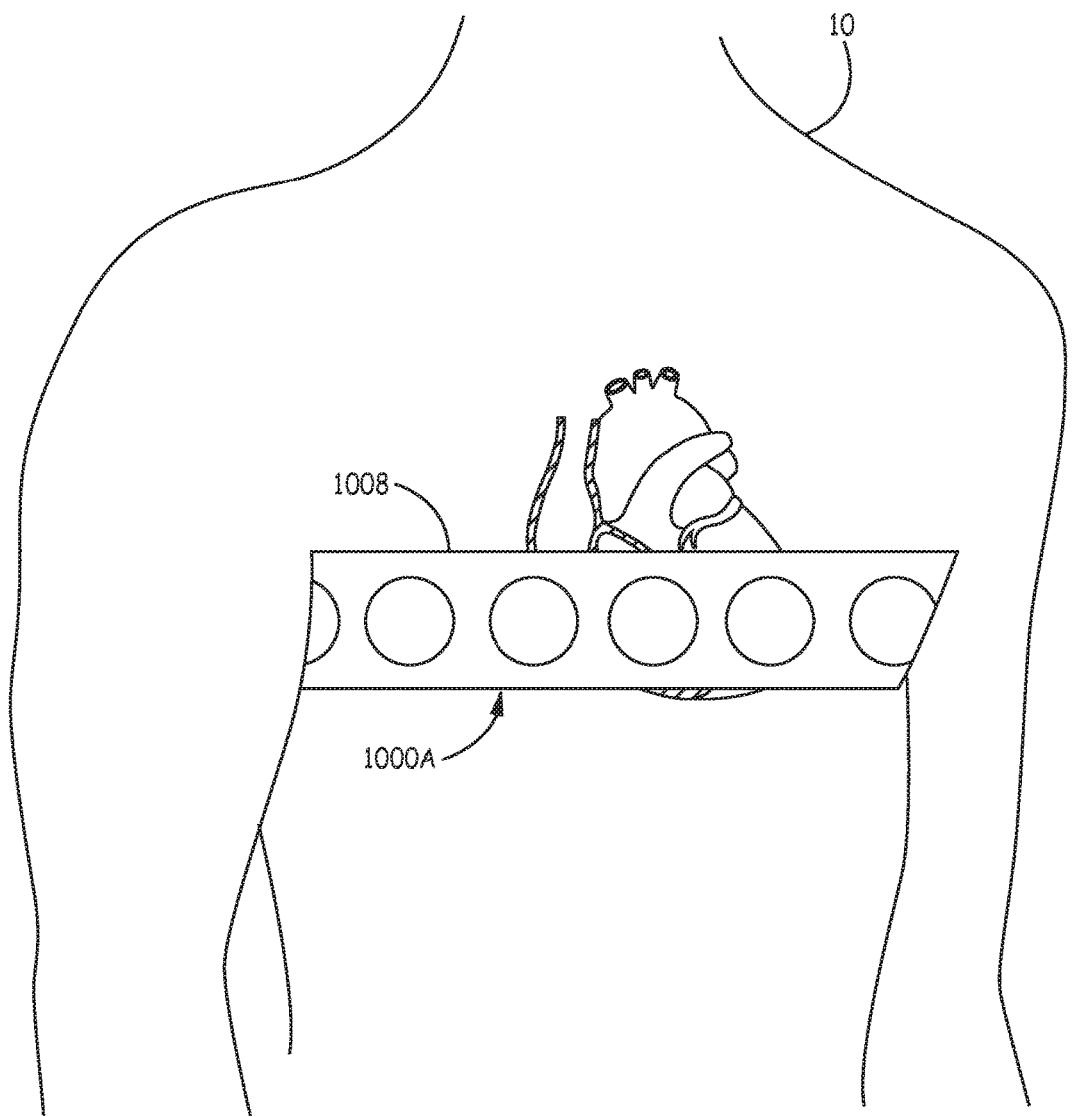
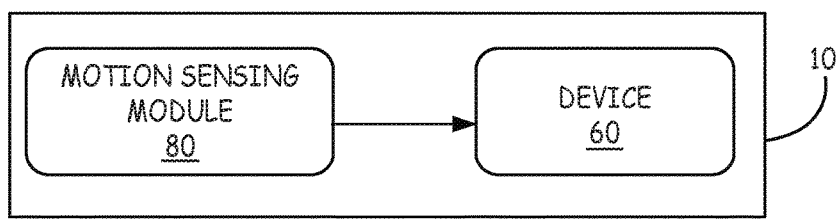
FIG. 11B

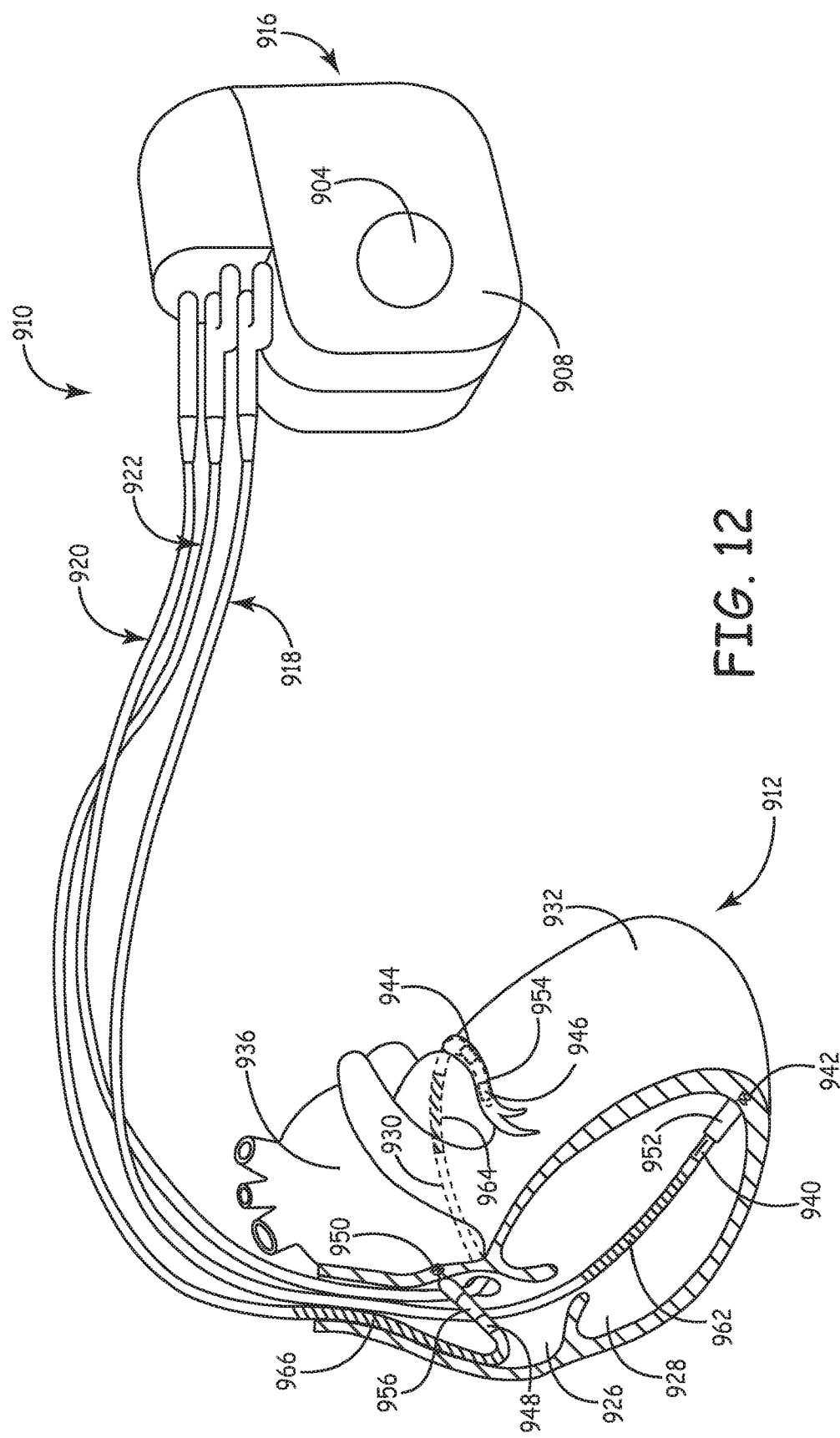

DETERMINING ONSETS AND OFFSETS OF CARDIAC DEPOLARIZATION AND REPOLARIZATION WAVES

RELATED APPLICATION

This application is a continuation of U.S. patent application Ser. No. 14/853,640 filed Sep. 14, 2015 entitled "DETERMINING ONSETS AND OFFSETS OF CARDIAC DEPOLARIZATION AND REPOLARIZATION WAVES" which is a continuation of Ser. No. 13/952,076, filed Jul. 26, 2013 entitled "DETERMINING ONSETS AND OFFSETS OF CARDIAC DEPOLARIZATION AND REPOLARIZATION WAVES", herein incorporated by reference in its entirety.

TECHNICAL FIELD

The invention relates to medical devices, and more particular, to medical devices for sensing, detection, and analysis of cardiac electrograms and electrocardiograms.

BACKGROUND

Implantable medical devices (IMDs), such as implantable pacemakers, cardioverters, defibrillators, or pacemaker-cardioverter-defibrillators, provide therapeutic electrical stimulation to the heart. IMDs may provide pacing to address bradycardia, or pacing or shocks in order to terminate tachyarrhythmia, such as tachycardia or fibrillation. In some cases, the medical device may sense intrinsic depolarizations of the heart, detect arrhythmia based on the intrinsic depolarizations (or absence thereof), and control delivery of electrical stimulation to the heart if arrhythmia is detected based on the intrinsic depolarizations.

IMDs may also provide cardiac resynchronization therapy (CRT), which is a form of pacing. CRT involves the delivery of pacing to the left ventricle, or both the left and right ventricles. The timing and location of the delivery of pacing pulses to the ventricle(s) may be selected to improve the coordination and efficiency of ventricular contraction.

IMDs sense signals and deliver therapeutic stimulation via electrodes. Implantable pacemakers, cardioverters, defibrillators, or pacemaker-cardioverter-defibrillators are typically coupled to one or more subcutaneous electrodes or intracardiac leads that carry electrodes for cardiac sensing and delivery of therapeutic stimulation. The signals sensed via the electrodes may be referred to as a cardiac electrogram (EGM) and may include the depolarizations, repolarizations, and other intrinsic electrical activity of the heart.

Systems for implanting medical devices may include workstations or other equipment in addition to the medical device itself. In some cases, these other pieces of equipment assist the physician or other technician with placing the intracardiac leads at particular locations on the heart. In some cases, the equipment provides information to the physician about the electrical activity of the heart and the location of the intracardiac lead. The equipment may perform similar functions as the medical device, including delivering electrical stimulation to the heart and sensing the depolarizations of the heart. In some cases, the equipment may include equipment for obtaining an electrocardiogram (ECG) via electrodes on the surface of the patient. In addition, the patient may have a plurality of electrodes on an ECG belt or vest that surrounds the torso of the patient. After the vest has been secured to the torso, a physician can perform a series of tests to evaluate a patient's cardiac response. The evaluation process can include detection of a baseline rhythm in which no electrical stimuli is delivered to cardiac tissue and another rhythm after electrical stimuli is delivered to the cardiac tissue. During the evaluation process, a physician typically needs to review the onset of cardiac depolarization waves in the rhythms. Reliable detection of depolarization waves assists the physician in setting parameters for optimal delivery of CRT. However, most algorithms require threshold detection of the depolarization signal or its derivative. Threshold detection may not reliably and consistently detect onset of cardiac depolarization for all patients and there may be inherent non-physiologic (e.g. noise) variations in thresholded parameters like slopes, amplitudes etc. from one cardiac cycle to another. It is therefore desirable to develop methods and systems of determining onset of cardiac depolarization waves in signals without the use of threshold detection.

BRIEF DESCRIPTION OF DRAWINGS

FIGS. 11B-11C are conceptual diagrams illustrating exemplary systems for measuring torso-surface potentials.

FIG. 12 is a conceptual diagram illustrating the implantable medical device (IMD) and leads of the system shown in FIG. 11A in greater detail.

DETAILED DESCRIPTION

The techniques and methods described in this disclosure allow a system to determine the onsets and offsets of heart depolarization waves and/or repolarization waves during the process of implanting the implantable medical device (IMD) or post-implant (e.g. periodic medical check-ups after the device has been implanted).

Figure 15:
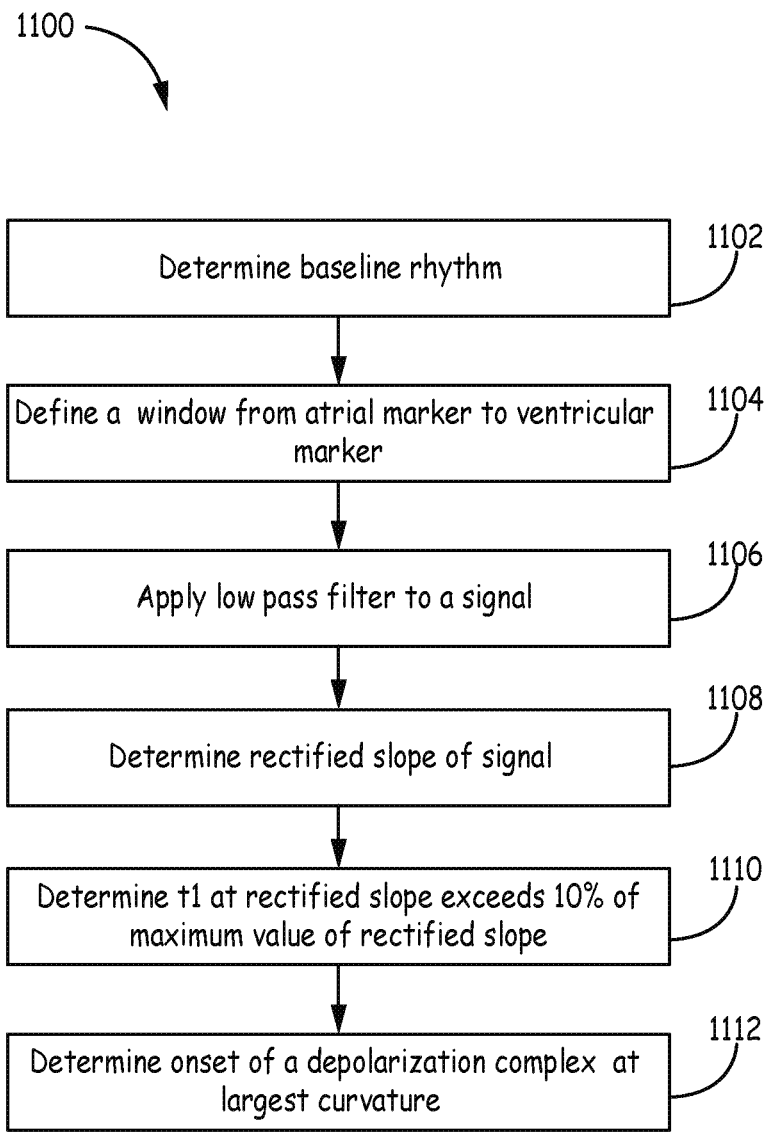
FIG. 15 is a flow diagram illustrating an example technique for detection of onset of heart depolarization waves.
Figure 16A:
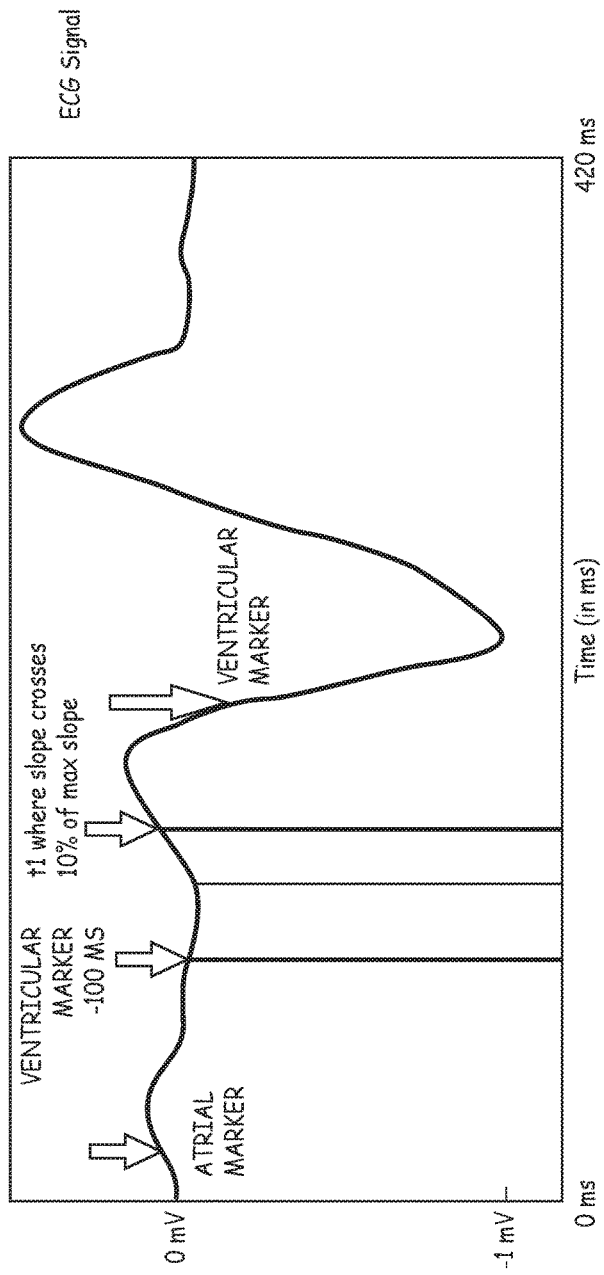
FIG. 16A is graphically depicts a cardiac ECG signal.

A computer-implemented method, embodied in FIG. 15, is directed to detection of onset of depolarization on far-field electrograms (EGMs), electrocardiograms (ECG)-or ECG-like signals. An ECG-like signal can be for example, a far-field intracardiac electrogram obtained from a device or invasively measured using a mapping wire inside the heart or it can be a leadless ECG generated by an implantable medical device. The method includes determining a baseline rhythm using a plurality of body-surface electrodes. The baseline rhythm includes an atrial marker and a ventricular marker. The atrial marker is associated with an atrial event while a ventricular marker is associated with a ventricular event. Each marker can be displayed to a user on a graphical user interface of a computer such as a programmer. A pre-specified time-window is defined as being between the timing of the atrial marker and timing of the ventricular marker. A low pass filter is then applied to a signal (usually a ECG signal or surrogate of an ECG signal like a far-field EGM, leadless device ECG, etc.) within the window. A rectified slope of the signal within the window is determined. A determination is then made as to whether a time point (t1) is present such that the rectified slope exceeds 10% of a maximum value of the rectified slope. A point of onset of a depolarization complex in the signal is then determined. The point of onset occurs at a largest curvature in the signal within the window from the voltage of the signal of the ventricular marker (Vs)-100 ms to t1, as shown in FIG. 16A. Vs refers to the timing of a ventricular event, for example ventricular sensing, as detected by the sensing circuits within the IMD. A curvature is defined as $r=|y''|/(1+|y'|^2)^{(3/2)}$ in which y" and y' are the double and single derivatives of a time varying signal y respectively where the time-varying signal is the signal acquired from surface electrodes and/or electrodes associated with an implanted medical device. The first and second derivatives of y can be determined using a variety of known methods. For example, the first derivative, y', can be determined based on finite difference methods (e.g. difference between successive time samples). The second derivative, y" can be similarly calculated but instead of using y, different points along y' curve are used.

In some examples, the diagnostic metrics may be used to optimize or otherwise guide the configuration of therapy, such as cardiac resynchronization therapy (CRT). For CRT, lead placement, pacing electrode configuration, or various atrio-ventricular or interventricular intervals may be configured based on metrics that are determined based on the identified onsets and/or offsets. In some examples, electromechanical delay may be used to configure CRT and, particularly, to select a lead placement, e.g. left-ventricular lead placement, during implantation of a CRT system.

In general, a heart produces a repetitive electrical signal which causes the heart to mechanically contract, thereby pumping blood throughout the body. Generally, the signal may be detected and displayed as a cardiac electrogram signal. Although the exact representation may differ depending on the placement of leads on or within the body to detect the heart signal, among other factors, a common cardiac electrogram includes several recognizable features. The initial deflections of the signal represent the P-wave and the QRS complex. The P-wave represents the depolarization of the atria and the QRS complex represents the depolarization of the ventricles. The Q-wave of the QRS complex is the initial downward deflection of the signal during the complex. Following the Q-wave is the R-wave, which is an upward deflection of the signal. Finally, the S-wave is another downward deflection. The next portion of the signal represents repolarization of the atria and ventricles. More specifically, what is generally called the T-wave represents the repolarization of the ventricles. There is no specific wave or feature of the signal that represents the repolarization of the atria because the generated signal is small in comparison to the T-wave. Together, the P-wave, the Q, R, and S waves, and the T-wave represent the depolarization and repolarization waves of a heart electrical signal.

The described techniques may enhance the accuracy of determining the onsets and offsets of the various waves which comprise the repeated cardiac electrogram signal. In particular, knowing more accurately the timing of the onsets and offsets of the waves allows for a more accurate determination of the electrical-electrical delays and the electromechanical delays. For example, the point of onset of ventricular depolarization on surface ECG forms a fiducial element (also simply referred to as "fiducial" or marker) with respect to which local electrical activation or depolarization times and may be measured at different sites in the ventricle. During implant of a heart lead for cardiac resynchronization therapy, the time-interval between this onset point and the time of local activation or depolarization at a candidate implant site within the ventricle may be evaluated and if it exceeds a certain threshold (e.g. 90 ms), that site may be selected for implant.

Skilled artisans appreciate that a fiducial element may include one or more of a ventricular event (e.g., a ventricular pace, a ventricular sense, etc.), an atrial event 32 a maximum value (e.g., a peak of a QRS complex, a peak of a P-wave, a peak of a Q wave, a peak of a R wave, etc.), a minimum value, a maximum slope value (e.g., a maximum slope of an R-wave, etc.), an amplitude or slope of atrial or ventricular depolarization signal, a crossing of a predefined threshold, etc. The timing of recurring fiducial element, or time when the recurring fiducial occurs, may be used to base the portion of the signal upon. For example, the start of fiducial element may start the time frame or window to store a portion of the signal. A 250 ms portion of the signal starting from a ventricular pace (i.e., the selected fiducial element) may be stored into memory. As such, a first portion may be recorded, or stored, from the start of a ventricular pace for 250 ms during a first a cardiac cycle, and a second portion may be recorded, or stored, from the start of a ventricular pace for 250 ms during a second cardiac cycle that is subsequent to the first cardiac cycle.

Figure 1:
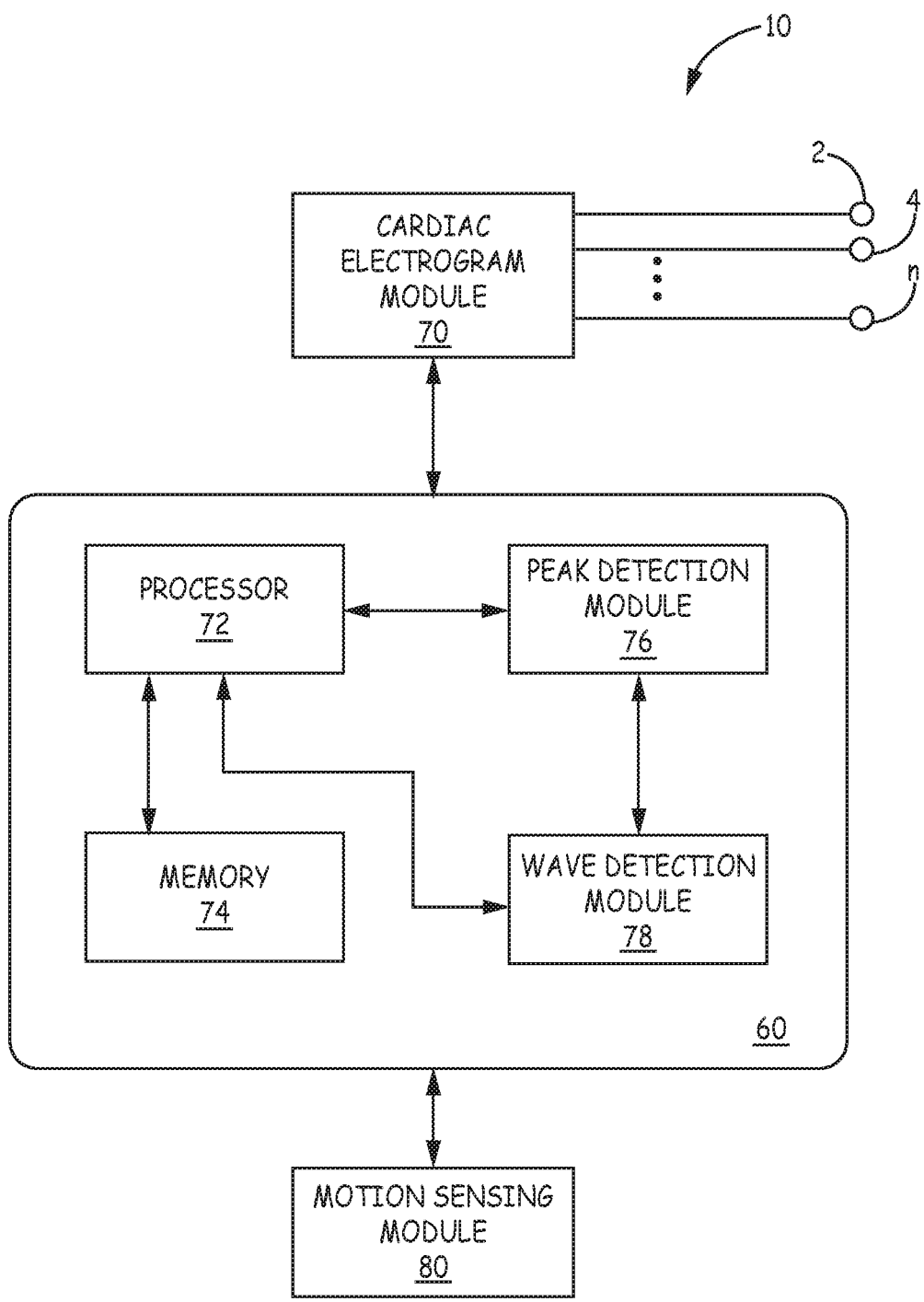
FIG. 1 is a block diagram illustrating and example system that may determine the onsets and offsets of various heart repolarization and depolarization waves.

FIG. 1 is a block diagram illustrating an example configuration of a system for determining the onsets and offsets of heart depolarization and repolarizations waves. In the illustrated example, system 10 includes a device 60, a cardiac electrogram module 70, and a motion sensing module 80. Device 60 may further include a processor 72, a memory 74, a peak detection module 76, and a wave detection module 78.

Processor 72 may include any one or more of a microprocessor, a controller, a digital signal processor (DSP), an application specific integrated circuit (ASIC), a field-programmable gate array (FPGA), or equivalent discrete or analog logic circuitry. In some examples, processor 72 may include multiple components, such as any combination of one or more microprocessors, one or more controllers, one or more DSPs, one or more ASICs, or one or more FPGAs, as well as other discrete or integrated logic circuitry. The functions attributed to processor 72 herein may be embodied as software, firmware, hardware or any combination thereof. Generally, processor 72 controls cardiac electrogram module 70, peak detection module 76, wave detection module 78, and motion sensing module 80 to determine timings of the onsets and offsets of heart depolarization and repolarizations waves.

Memory 74 includes computer-readable instructions that, when executed by processor 72, causes system 10 and processor 72 to perform various functions attributed to system 10 and processor 72 herein. Memory 74 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media.

Generally, cardiac electrogram module 70 is configured sense or acquire electrical signals from a patient. Cardiac electrogram module 70 is electrically coupled to one or more electrodes 2, 4, 6, 8, 10, 12, 14 . . . n by one or more leads. In some examples, the one or more electrodes 2, 4, 6, 8, 10, 12, 14 . . . n may be external electrodes, e.g., attached to the surface of a patient, or implanted at various locations within a patient, e.g., on or within a heart.

Figure 2:
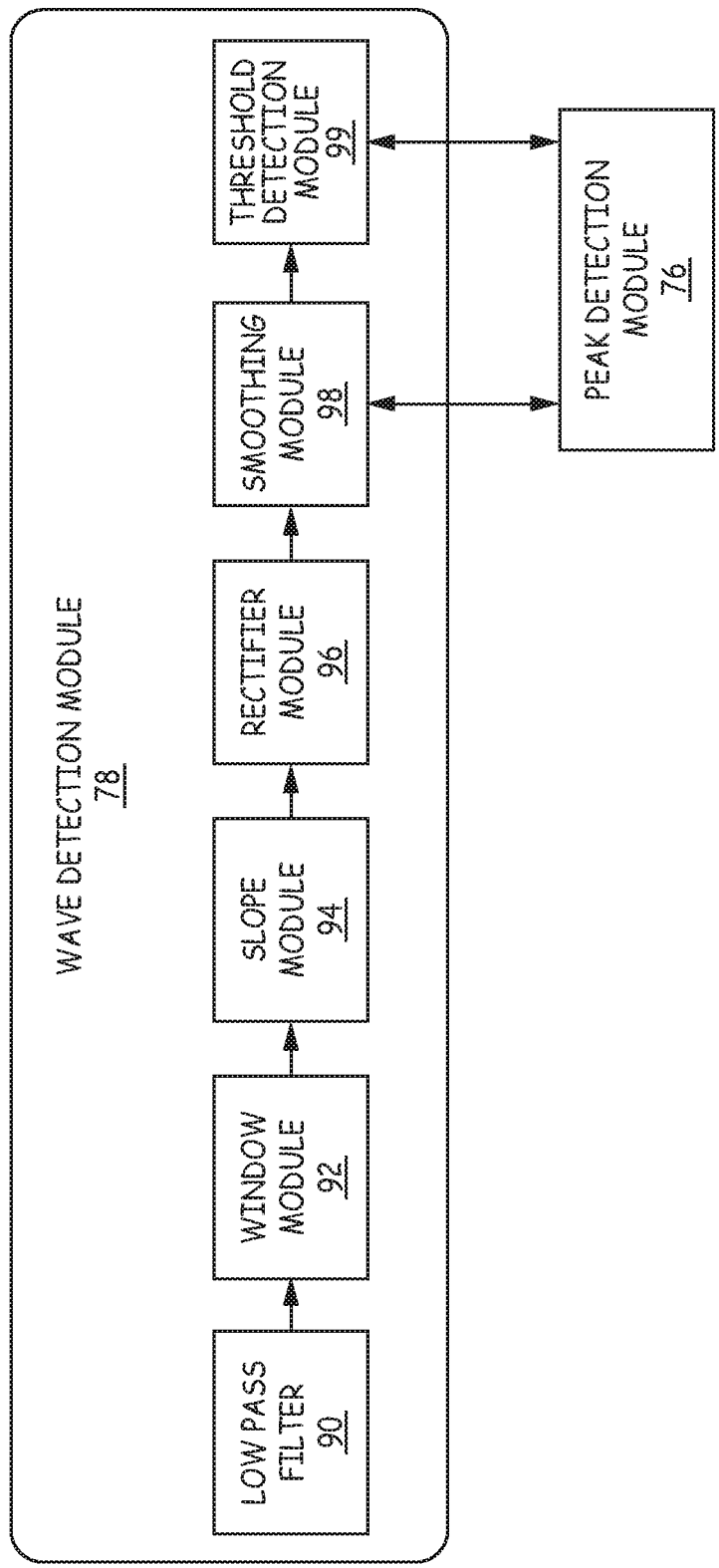
FIG. 2 is a block diagram illustrating an example configuration of a wave detection module.

Peak detection module 76 may be configured to determine a maximum value of a particular signal. For example, peak detection module 76 may be configured to receive the electrical signal from cardiac electrogram module 70 and determine the maximum value. In another example, as illustrated in FIG. 2, peak detection module 76 may be configured to receive a signal from wave detection module 78 and determine a maximum value.

Wave detection module 78 determines the onsets and offsets on the heart depolarization and repolarizations waves. Wave detection module 78 may be configured to receive an electrical signal. For example, wave detection module 78 may be configured to receive an electrical signal sensed by cardiac electrogram module 70. Motion sensing module 80 may detect mechanical motion of a heart, e.g., during contraction of the heart. Motion sensing module 80 may comprise one or more sensors that generate a signal that varies based on cardiac contraction or motion generally, such as one or more accelerometers, pressure sensors, impedance sensors, or flow sensors. Motion sensing module 80 may provide an indication of the timing of motion, e.g., contraction, to device 60, e.g., to processor 72. The detected contraction may be contraction of cardiac tissue at a particular location, e.g., a particular portion of a ventricular wall.

In some examples, motion sensing module 80 may be configured to image the heart, or electrodes, catheters, wires, or other radio-opaque markers in or on the heart and identify motion associated with contraction based on images of the heart. In some examples, motion sensing module 80 may be configured to direct ultrasound energy toward a patient's heart. Motion sensing module 80 may also be configured to detect any ultrasonic energy deflected back toward motion sensing module 80 by the patient's heart. In this manner, motion sensing module 80 may capture information about the mechanical motion (i.e. the contracting and relaxing of the ventricles and/or atria) of the heart. Systems and methods for identifying heart mechanical contractions are described in U.S. Pat. No. 7,587,074 to Zarkh et al., which issued on Sep. 8, 2009 and is entitled, "METHOD AND SYSTEM FOR IDENTIFYING OPTIMAL IMAGE WITHIN A SERIES OF IMAGES THAT DEPICT A MOVING ORGAN," and is incorporated herein by reference in its entirety.

Processor 72 may determine values of one or more metrics, such as cardiac intervals or cardiac electromechanical delay, based on the timing of onset and/or offset of a wave, as determined by wave detection module 78, and/or the timing of contraction, as determined by motion sensing module 80. For example, processor 72 may determine QRS width based on an onset and offset of the QRS complex as identified by wave detection module 78. As another example, processor 72 may determine a QT interval based on a QRS onset and T-wave onset identified by wave detection module 78. The processor may also determine the interval between the onset of depolarization on a surface ECG lead and the time of local electrical activation as sensed by a lead or a mapping catheter or guidewire at a site within the heart. Furthermore, as described in greater detail below, processor 72 may determine electromechanical delay based on a QRS onset identified by wave detection module 78 and an indication of the timing of cardiac contraction received from motion sensing module 80.

Figure 13:
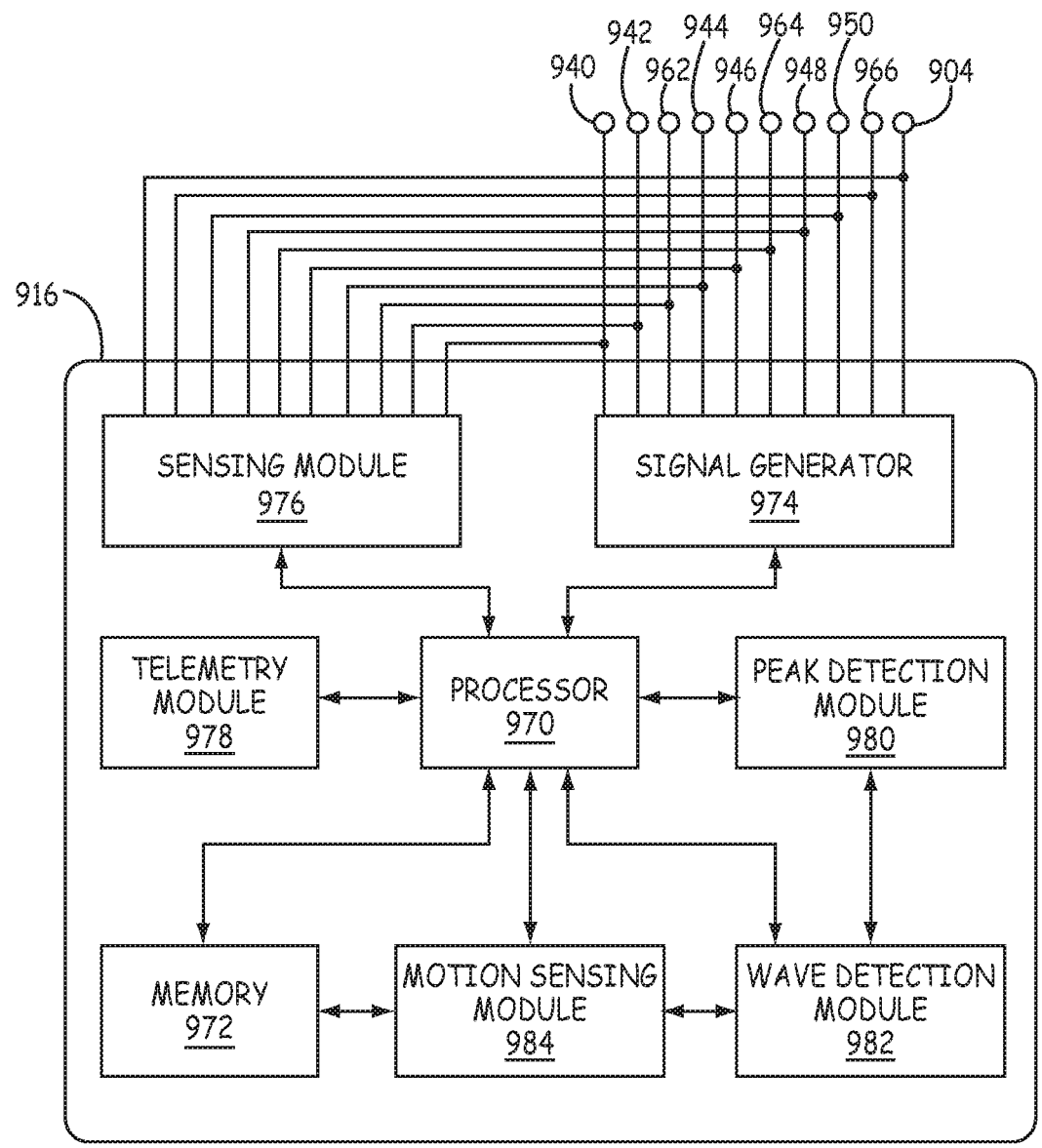
FIG. 13 is a block diagram of an example implantable medical device that may determine the onset and offset of heart depolarization and repolarization waves.

Although in FIG. 1 device 60, module 70, and module 80 are depicted as separate, in other examples the modules and device may be combined into fewer separate components. For example, as illustrated in FIG. 13, all of the functionality of system 10 may be combined into a single device.

Furthermore, although processor 72, peak detection module 76 and wave detection module 78 are depicted as separate functional modules in the example of FIG. 1, their collective functionality may be provided by any number of physical or logical processing elements provided by one or more co-located or networked devices. In one example, peak detection module 76 and wave detection module 78 may be functional modules executed by processor 72. Similarly in FIG. 2, although the various modules 90, 92, 94, 96, 98, and 99 are depicted as separate modules in a single device, in other examples their functionality may be provided by any one or more devices.

FIG. 2 is a block diagram illustrating an example configuration of wave detection module 78. In the example of FIG. 2, wave detection module 78 comprises a low-pass filter 90, a window module 92, a slope module 94, a rectifier module 96, a smoothing module 98, and a threshold detection module 99.

Low pass filter 90 may generally be any low-pass filter designed to reduce or eliminate the high frequency components of electrical signals. Some examples of low-pass filters embodied in hardware include capacitive low-pass filters and inductive low-pass filters. Other low-pass filters may be embodied entirely within software. In some embodiments, low-pass filter 90 is embodied as a combination of hardware and software. Low-pass filter 90 may be a first, second, or higher order filter. In some examples, low-pass filter 90 comprises multiple filters placed in a succession in order to create a desired frequency response. In some examples, the low-pass filter 90 is a linear filter with a maximally flat group delay or maximally linear phase response. A constant group delay is a characteristic of phase response of an analog or a digital filter, which helps preserve the shape of the signal in the pass-band. In at least one example, the low-pass filter is a Bessel filter with a cut-off frequency of 15 Hz.

Window module 92 may generally window received signals. In some examples, window module 92 may receive cardiac electrograms, and in further examples, some of the cardiac electrograms may include a marker or markers indicating one or more points of interest. Some example of points of interest could be the R-wave, the P-wave, or any other wave of the cardiac electrogram. In some examples, peak detection module 76 may detect the locations of R-waves in a cardiac electrogram, according to techniques that are well known in the art, for example using a varying threshold. Peak detection module 76 may then place a marker within the cardiac electrogram identifying the location of the R-wave. In other examples, other modules or devices may detect and mark waves in the cardiac electrogram. In examples where the signal includes at least one marker, window module 92 may window the received electrical signal around the marker. For example, window module 92 may multiply the received electrical signal by zero outside of the area around the marker and by one inside of the area around the marker. In this way, window module 92 may modify the received electrical signal to only contain information in an area around the marker. In some examples, window module 92 may isolate the QRS complex. In some examples, window module 92 may window an area of interest of equal length around the marker, for instance 150 ms before the marker and 150 ms after the marker. In other examples, the area in front of the marker may be longer or shorter than the area behind the marker.

Slope module 94 may generally determine the slope of a received electrical signal. Some example techniques for determining a slope that slope module 94 may use are taking the simple difference between adjacent points on the received electrical signal, or determining the first derivative of the received electrical signal.

Rectifier module 96 may generally rectify a received electrical signal. For example, rectifier module 96 may half-wave rectify the received electrical signal to produce a resulting signal with information only where the original signal was above zero. In another example, rectifier module 96 may full-wave rectify the received electrical signal to produce a resulting signal where all the negative values of the original signal are now positive.

Smoothing module 98 may generally smooth a received electrical signal. For example, smoothing module 98 may be configured to increase the values of certain points and decrease the values of certain points so as to create a smoother signal. Some example smoothing algorithms include rectangular or un-weighted sliding average smoothing, triangular smoothing, and Savitzky-Golay smoothing. The smoothing algorithms may be implemented through one or more filters. In at least one example, the smoothing filter is 10-order median filter. In another example, the smoothing filter is a n-order median filter where n is an increasing linear function of the sampling frequency used to digitize the electrogram or electrocardiogram signals.

Threshold detection module 99 may generally be configured to determine a threshold and at what points a received electrical signal crosses a pre-determined threshold. The threshold may be determined based on a maximum value of the signal received from smoothing module 98. For example, as illustrated in FIG. 2, threshold detection module 99 may be configured to receive, from peak detection module 76, a maximum value of the signal received from smoothing module 98. Threshold detection module 99 may be configured to determine a threshold value based on the received maximum value. For example, threshold detection module 99 may determine the threshold to be ten percent, fifteen percent, twenty percent, or more of the maximum value. Ultimately, threshold detection module 98 may determine the onsets and offsets of heart depolarization and repolarizations waves based on at which points of a received electrical signal cross a threshold.

Figure 3:
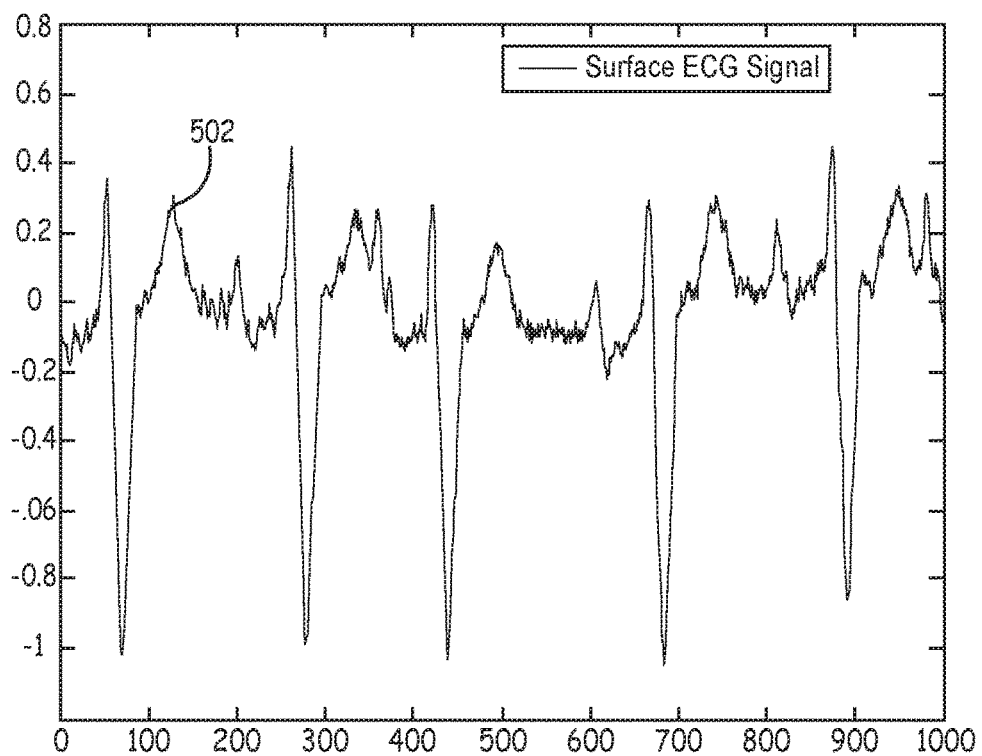
FIG. 3 is a graph illustrating an example cardiac electrogram.
Figure 4:
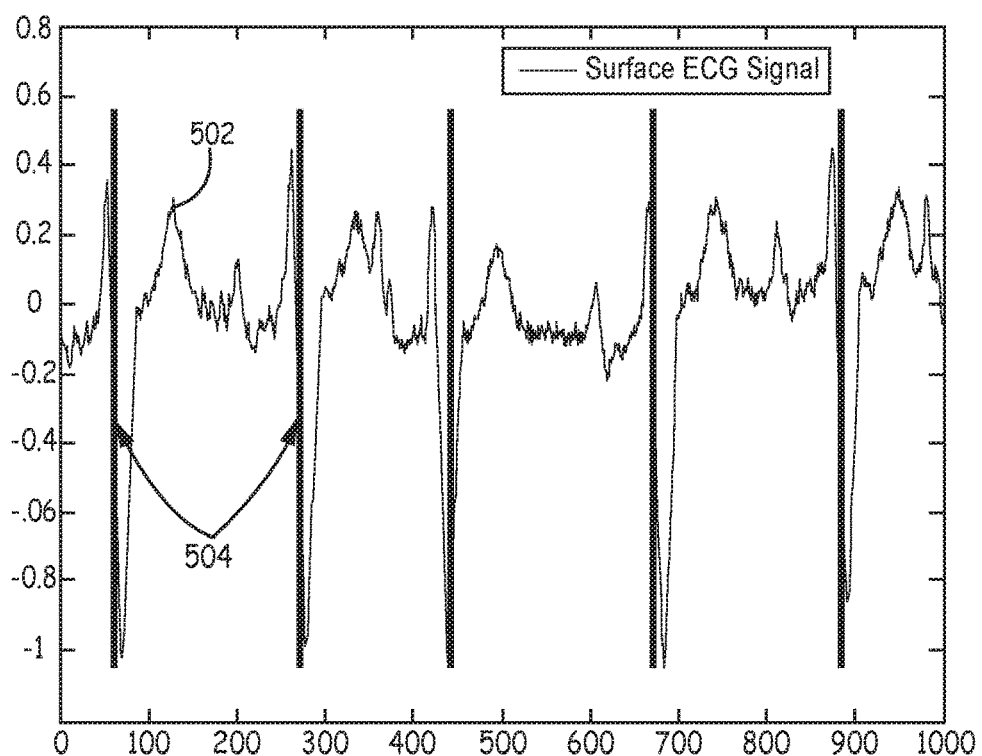
FIG. 4 is a graph illustrating an example cardiac electrogram including R-wave marker information.
Figure 5:
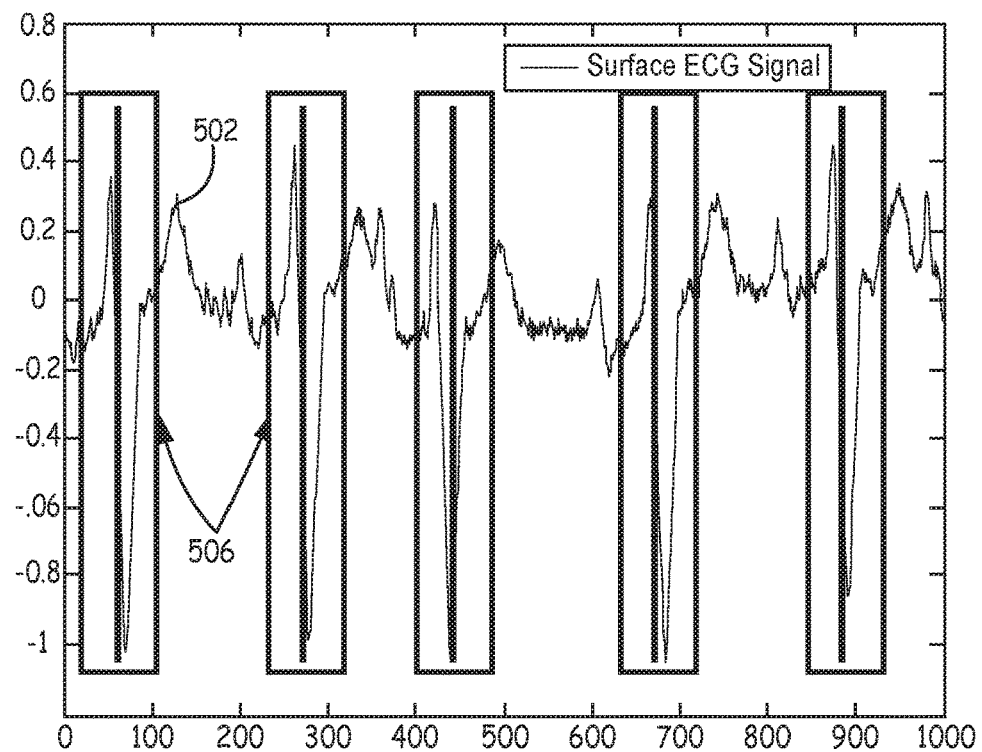
FIG. 5 is a graph illustrating an example cardiac electrogram including R-wave marker information and example windows around each marker.
Figure 6:
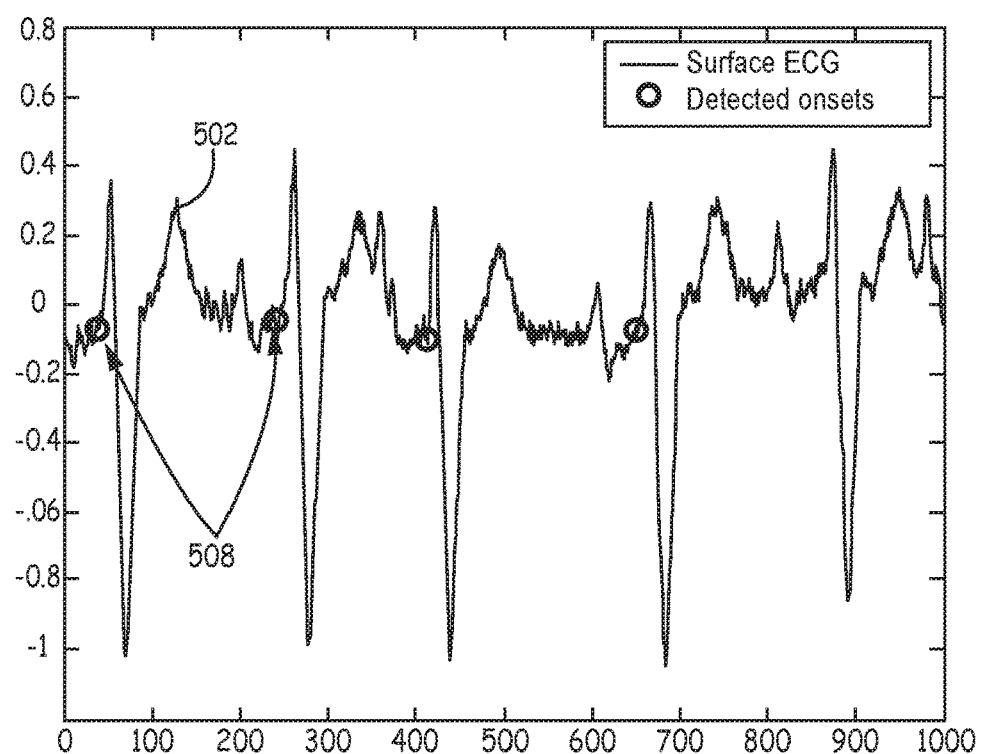
FIG. 6 is a graph illustrating an example cardiac electrogram including example determined wave onset points.

FIGS. 3-6 illustrate example cardiac electrogram signals along with various aspects of the present disclosure. For example, FIG. 3 illustrates an example cardiac electrogram 502 that may be passed to wave detection module 78. FIG. 4 illustrates a cardiac electrogram 502 along with wave markers 504. In the example of FIG. 4, wave markers 504 are R-wave markers. FIG. 5 also depicts an example cardiac electrogram 502 and R-wave markers 504. FIG. 5 also depicts example windows 506 that wave detection module 78, e.g. through window module 92, may generate about the wave markers 504. In the example of FIG. 5, windows 506 are configured to generally include the QRS complexes and isolate the QRS complexes from the whole cardiac electrogram, e.g. exclude other waves such as the P-wave and T-wave. In other examples, the windows 506 may be configured to generally include P or T-waves and isolate those waves from the whole cardiac electrogram. FIG. 6 further illustrates an example cardiac electrogram 502. FIG. 6 also illustrates the points that wave detection module 78 has determined are the onset of the waves (more specifically, in the example illustrated in FIG. 6, the onset of the QRS waves).

Figure 7:
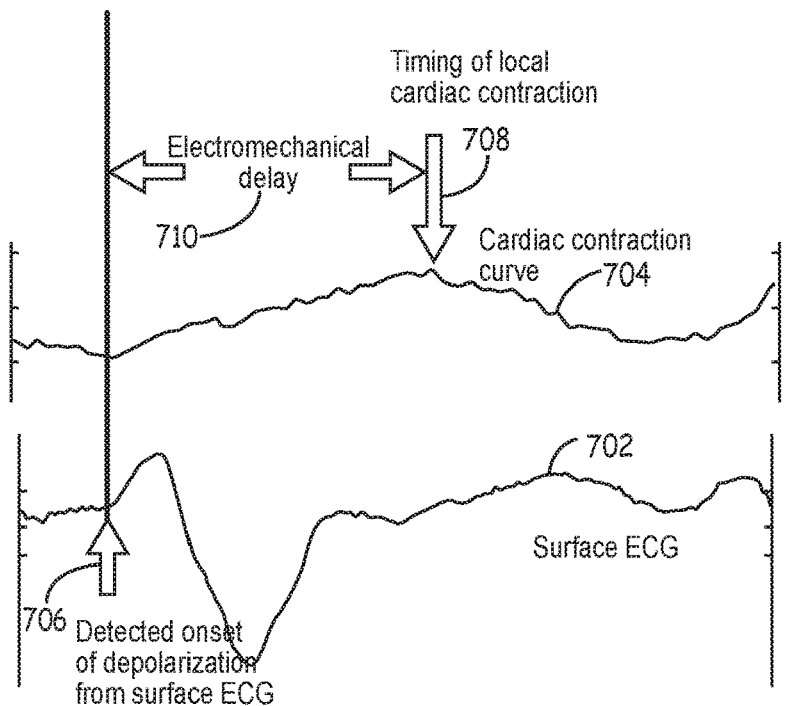
FIG. 7 is a graph illustrating both a cardiac contraction curve and a surface ECG curve with indicators marking the determined onset of depolarization of the heart and the detected timing of local heart mechanical contraction.
Figure 8:
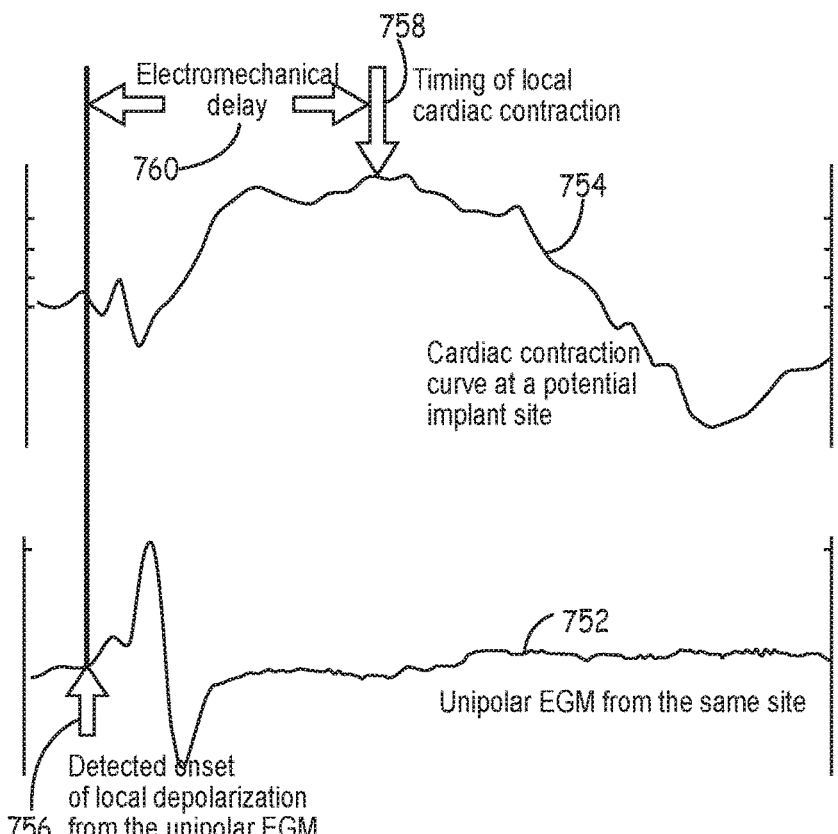
FIG. 8 is a graph illustrating both a cardiac contraction curve at a potential intracardiac lead implant site and a local EGM curve from the same potential implant site with indicators marking the determined onset of local depolarization of the heart and the detected timing of local heart mechanical contraction.

FIGS. 7 and 8 illustrate example cardiac electrograms combined with example heart mechanical contraction information. For example, FIG. 7 depicts an example surface ECG signal 702 along with a cardiac contraction curve 704. Cardiac contraction curve 704 illustrates the contraction of a local point on the heart with respect to time. The cardiac contraction curve may be a signal generated by any of the sensors discussed above, for example accelerometers, pressure sensors, impedance sensors, or flow sensors associated with motion sensing module 80. In other examples, the cardiac contraction curve may be generated by the techniques described in the U.S. Pat. No. 7,587,074 to Zarkh et al., which issued on Sep. 8, 2009 and is entitled, "METHOD AND SYSTEM FOR IDENTIFYING OPTIMAL IMAGE WITHIN A SERIES OF IMAGES THAT DEPICT A MOVING ORGAN," incorporated herein. In still other examples, the cardiac contraction curve may be generated by sensors within the tip of an intracardiac electrode. For example, the tip of a cardiac electrode may contain one or more motion sensors which generates a signal as the tip of the electrode moves in relation to the region of the heart in which it is implanted.

Also depicted in FIG. 7 are the timing of the detected onset of depolarization of the heart from the surface ECG 706 and the timing of the local cardiac contraction 708. The delay between the onset of depolarization 706 from the surface ECG and the timing of local cardiac contraction 708 may be described as the global electromechanical delay 710. As will be described in greater detail in FIGS. 9-10, measuring the global electromechanical delay 710 delay at various locations on the heart may help physicians to select potential intracardiac lead implant sites.

FIG. 8 depicts an example unipolar cardiac electrogram signal 752 from an electrode at a localized position on or within a heart, along with a cardiac contraction curve 754 from the same localized position on or within the heart. FIG. 8 also depicts the timing of the detected onset of depolarization of the heart at the localized position 756 and the timing of the local cardiac contraction 758. In contrast to FIG. 7, FIG. 8 displays the difference in timing between the local depolarization of the heart 756 and the timing of the local cardiac contraction 758 as the local electromechanical delay 760 or local electromechanical latency 760. The local electromechanical delay 760 differs from the global electromechanical delay 710 in that local electromechanical delay 760 measures the differences in timings both at the localized heart tissue and the global electromechanical delay 710 measures the difference in timings between the depolarization 706 detected at the surface ECG and the local mechanical contraction 708.

Figure 9:
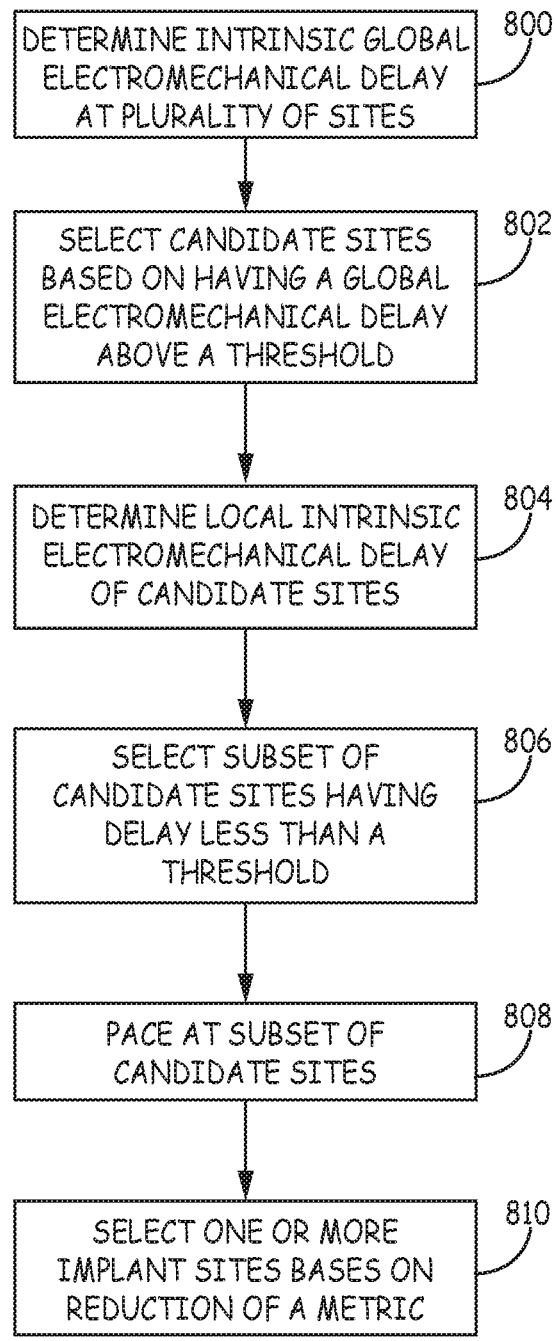
FIG. 9 is a flow diagram illustrating an example technique for selecting intracardiac lead implant sites.

FIG. 9 is a flow diagram describing an example method for selecting an implant site for an intracardiac lead. In the example method, a system, such as system 10 of FIG. 1, may determine the intrinsic global electromechanical delay at a plurality of potential intracardiac lead implant sites. To determine the intrinsic global electromechanical delay, a system may determine the timing of a detected onset of depolarization from a surface ECG and a timing of cardiac contraction at various locations on the heart during an intrinsic heart rhythm. The difference between the timings is the global electromechanical delay (800). Then, in the example technique, a system, e.g., processor 72, or a user of the system, may select candidate intracardiac lead implant sites as sites that have a global electromechanical delay above a certain threshold (802). Finding particular candidate sites with a long global electromechanical delay may indicate that the particular location of the heart contracts late and may be the reason for dyssynchrony of cardiac wall motion. Selecting an implant site to provide pacing on or near that site may enhance the effectiveness of the electrical pacing therapy to restore cardiac synchrony.

In the example technique, processor 72 may then determine the local electromechanical delay of the selected candidate implant sites during an intrinsic heart rhythm (804). To determine the local electromechanical delay, processor 72 may determine the timing of a detected onset of depolarization from an electrogram taken at the potential implant site and a timing of the local cardiac contraction at the potential implant sites. The local electromechanical delay is the difference between the determined timings. Then, in the example technique, processor 72 may automatically select a subset of potential implant sites as sites that have a local electromechanical delay less than a threshold (806). In other examples, a user may manually select the potential implants based on information from processor 72. Candidate implant sites that have a long local electromechanical delay may indicate a region of scarred or non-viable or otherwise non-conductive tissue. Implanting an intracardiac lead at those locations may reduce the effectiveness of the electrical stimulation therapy.

Processor 72 may then deliver electrical pacing stimulus to the heart at the potential implant sites (808). Processor 72 may measure various metrics such as global or local electromechanical delay during pacing at each potential implant site. In the example technique, processor 72 may then automatically select one or more implant sites based on the reduction of a metric during pacing compared to the intrinsic baseline. In other examples, a user may select one or more implant sites based on information from processor 72. For example, processor 72, or a user, may select one or more implant sites based on the reduction of local electromechanical, global electromechanical delay, or cardiac dyssynchrony, which is a measure of the distribution and dispersion (e.g. range, standard deviation, etc.) of global or local electromechanical delays at various cardiac sites. In other example techniques, processor 72 or a user may select other parameters based on the global and/or local electromechanical delay. For example, processor 72 may also vary parameters of the pacing, such as A-V delay, V-V delay, and pacing electrode configuration, and select a particular pacing electrode configuration or pacing intervals for cardiac resynchronization therapy based on the metric. In other examples, a user may ultimately select the pacing electrode configuration or pacing intervals based on the metric.

Figure 10:
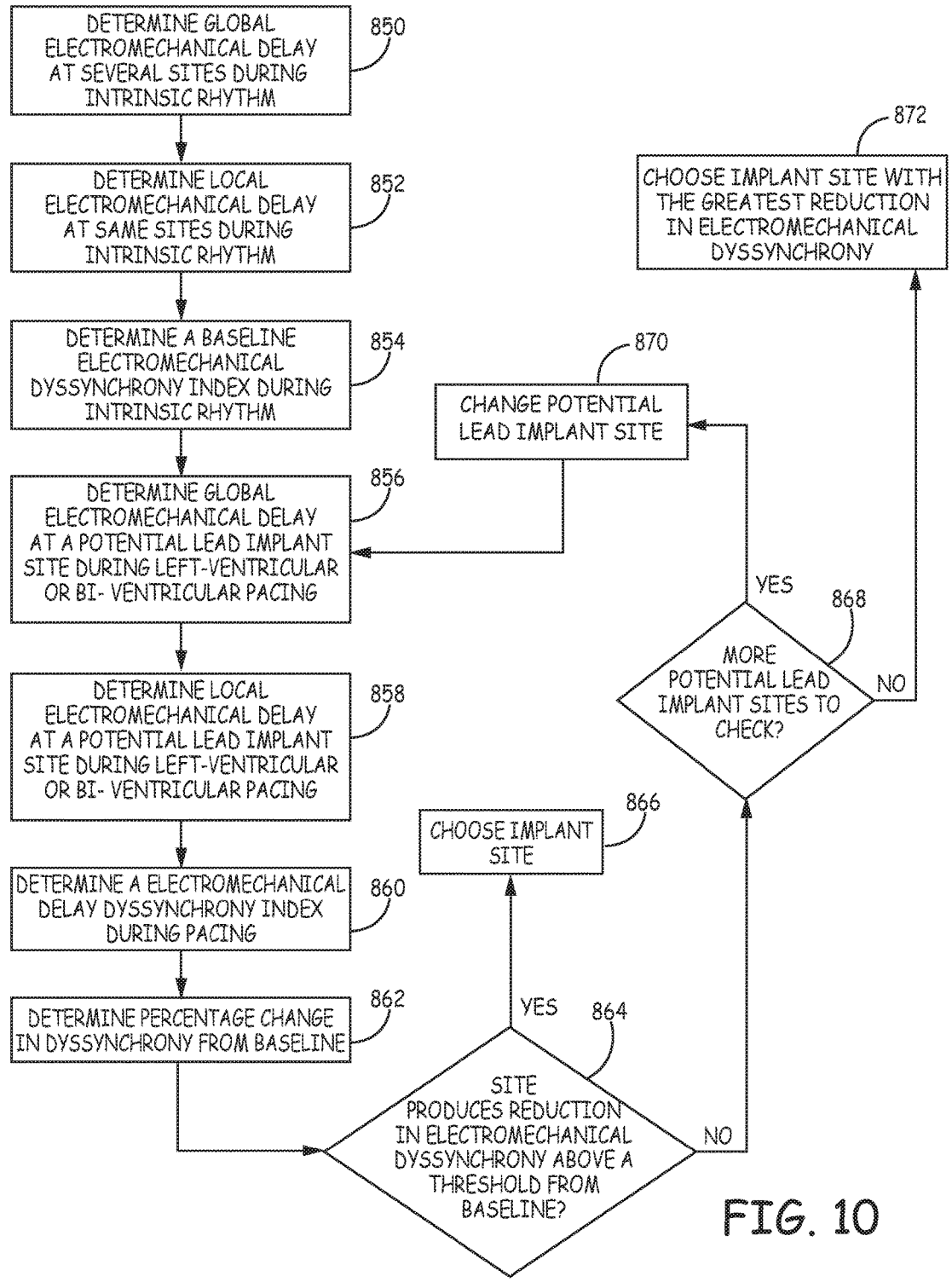
FIG. 10 is a flow diagram illustrating an example technique for selecting intracardiac lead implant site.

FIG. 10 is flow diagram illustrating another example technique for selecting an implant site for an intracardiac lead. In the example technique, a system, such as system 10, may determine a global electromechanical delay at a potential implant site during an intrinsic heart rhythm (850). In the example technique, a system may then determine local electromechanical delay at the same potential implant site during an intrinsic heart rhythm (852). A system may then determine a baseline electromechanical dyssynchrony index for an intrinsic heart rhythm (854). A system may determine the baseline electromechanical dyssynchrony index by comparing the differences between the global and local electromechanical delays during the intrinsic heart rhythm.

In the example technique, a system may then determine a global electromechanical delay at the same potential implant site during the delivery of electrical pacing therapy (856). In the example technique, a system may then determine local electromechanical delay at the same potential implant site during the delivery of electrical pacing therapy (858). A system may then determine an electromechanical dyssynchrony index during pacing therapy (860).

In the example technique, a system may then determine the percentage change between the baseline electromechanical dyssynchrony index and the electromechanical dyssynchrony index determined during pacing therapy (862). A system may then determine if there was a reduction from the baseline dyssynchrony index at the tested potential implant site above a threshold percentage (864). If the system determines that the performance of the pacing at the potential implant site did produce a reduction in the baseline electromechanical dyssynchrony index above a threshold percentage (YES of 864), the system may select that implant site (866) for intracardiac lead implantation. In some examples, a processor of the system, such as processor 72, may automatically select the implant site according to the described techniques. In other examples, a user, based on information from a processor may manually select the implant site according to the described techniques. If the system determines that pacing at the potential site did not reduce the baseline electromechanical dyssynchrony index by a threshold percentage amount (NO of 864), the system may check to see if there are other potential lead implant sites to check (868). If there are still other implant sites to check (YES of 868), in the example technique, a system may change the potential lead implant site (870) and return to step 856. If there are no more potential lead implant sites to check (NO of 868), a system may select the implant site with the greatest reduction in the baseline electromechanical dyssynchrony index as the preferred intracardiac lead implant site.

Figure 14:
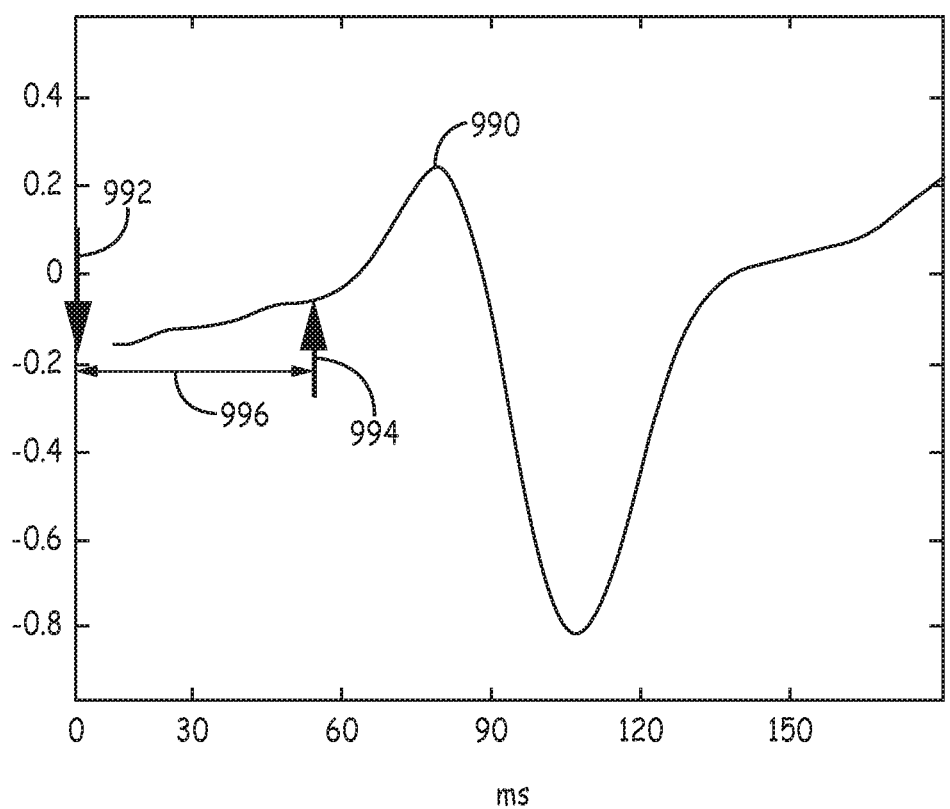
FIG. 14 illustrates an example of the time-delay between the delivery of pacing and the onset of depolarization.

In another example, the system may detect the time-interval from delivery of pace at a localized region within the heart to the onset of depolarization on a surface ECG lead, with the pace delivered at maximum pacing voltage (~6V to ensure that maximum energy is delivered during pacing) and at a short atrio-ventricular (A-V) interval (≤60 ms). If this time interval exceeds a certain threshold, then the system will indicate that particular area is not a suitable site for implanting the pacing lead. This is because a long time delay between delivery of local pace (at maximum energy) and onset of global depolarization on surface ECG indicates that the substrate of that area in the heart may be non-viable or otherwise not be a suitable site for implanting the pacing lead, e.g., comprised of scar tissue. FIG. 14 illustrates an example of the time-delay between the delivery of pacing and the onset of depolarization. FIG. 14 illustrates an example ECG signal 990. Arrow 992 points to the point in time when a patient received pacing at a localized region of the heart. Arrow 994 points to the determined point in time of the onset of the depolarization wave. The onset of the depolarization wave may be found, for example, according the techniques described in this disclosure. Time period 996 is the difference in time between the beginning of pacing and the onset of the depolarization wave at a localized region of the heart. The time period 996 may also be termed the local electrical-electrical delay.

Figure 11A:
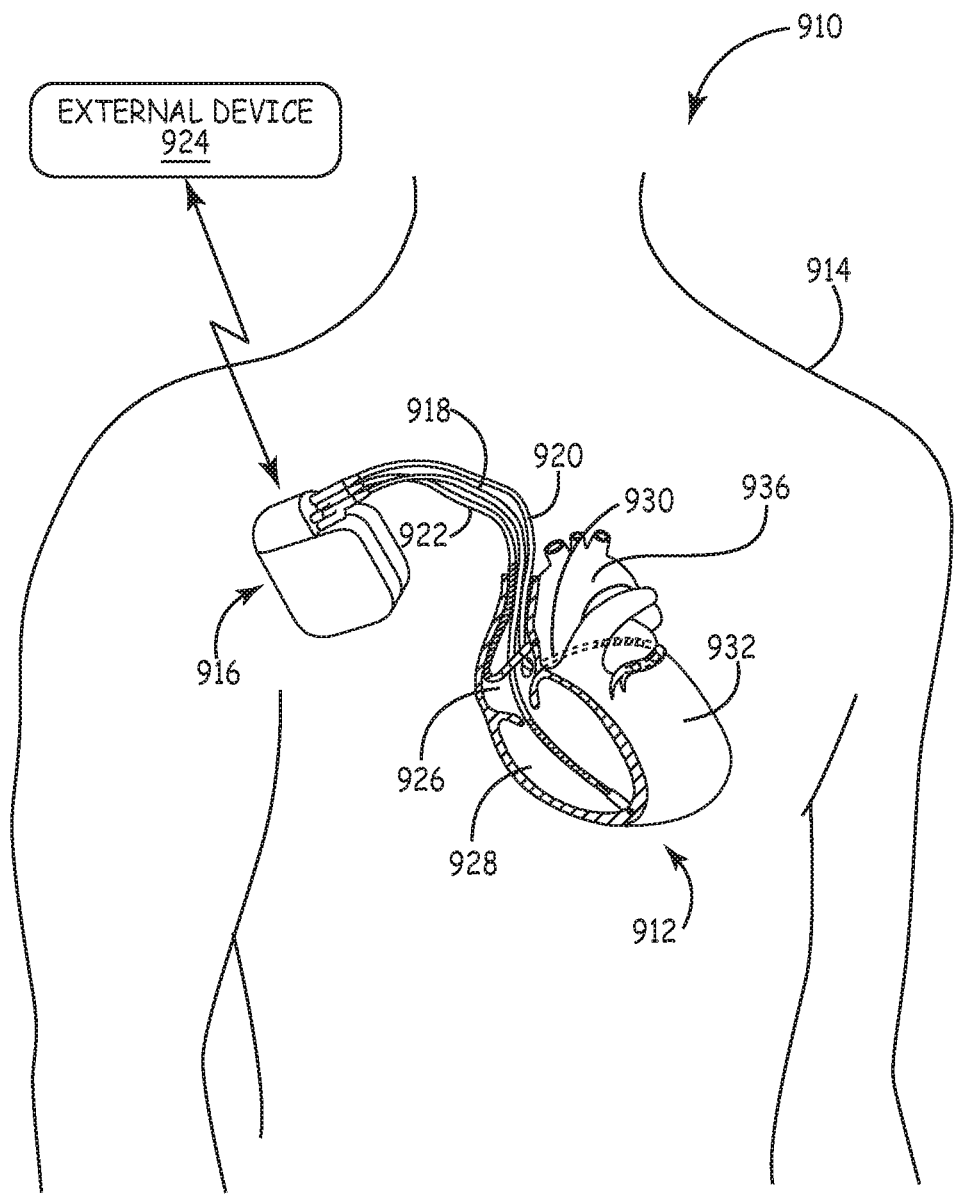
FIG. 11A is a conceptual diagram illustrating an example system that determines the onset and offsets of heart depolarization and repolarization waves.

FIGS. 11-13 are conceptual diagrams illustrating an example system 910 that determines the onset and offset points of heart depolarization and repolarization waves of patient 914 according to the techniques described herein. As with the previously described system, in one example, system 910 may detect the onset and offset points of heart depolarization and repolarization waves in order to select a preferred location for implanting an intracardiac lead. In other examples, system 910 may detect the onset and offset points of heart depolarization and repolarization waves in order to select other parameters based on the electromechanical delay. For example, the system may select a particular pacing electrode configuration or pacing intervals for cardiac resynchronization therapy. In another example, with multipolar leads offering choices of more than one pacing electrode (cathode) in the ventricle, the system/device may automatically pace from each of the pacing electrodes at maximum pacing voltage and at a nominal atrio-ventricular delay (~100 ms) and measure onsets and offsets of the resulting depolarization waveforms on a far-field electrogram or on a leadless ECG or on a surface ECG lead, and choose the pacing electrode which produces the minimum difference between the offset of the local electrogram and the corresponding far-field onset, for delivery of cardiac resynchronization therapy. Alternatively, the pacing electrode which produces the narrowest far-field electrogram or surface ECG signal calculated as the difference between the offset and onset could be chosen. As illustrated in example diagram FIG. 11A, a system 910 includes implantable medical device (IMD) 916, which is connected to leads 918, 920, and 922, and communicatively coupled to a programmer 924. IMD 916 senses electrical signals attendant to the depolarization and repolarization of heart 912, e.g., a cardiac EGM, via electrodes on one or more of leads 918, 920 and 922 or a housing of IMD 916. IMD 916 also delivers therapy in the form of electrical signals to heart 912 via electrodes located on one or more leads 918, 920, and 922 or a housing of IMD 916, such pacing, cardioversion and/or defibrillation pulses. IMD 916 may include or be coupled to various sensors, such as one or more accelerometers, for detecting other physiological parameters of patient 914, such as activity or posture.

In some examples, programmer 924 takes the form of a handheld computing device, computer workstation, or networked computing device that includes a user interface for presenting information to and receiving input from a user. A user, such as a physician, technician, surgeon, electrophysiologist, or other clinician, may interact with programmer 924 to communicate with IMD 916. For example, the user may interact with programmer 924 to retrieve physiological or diagnostic information from IMD 916. A user may also interact with programmer 924 to program IMD 916, e.g., select values for operational parameters of the IMD.

IMD 916 and programmer 924 may communicate via wireless communication using any techniques known in the art. Examples of communication techniques may include, for example, low frequency or radiofrequency (RF) telemetry, but other techniques are also contemplated. In some examples, programmer 924 may include a programming head that may be placed proximate to the patient's body near the IMD 916 implant site in order to improve the quality or security of communication between IMD 916 and programmer 924. In other examples, programmer 924 may be located remotely from IMD 916, and communicate with IMD 916 via a network.

The techniques for identifying onsets and/or offsets of cardiac electrogram waves may be performed by IMD 916, e.g., by a processor of IMD 916, based on one or more cardiac electrograms sensed by the IMD. In other examples, as described previously, some or all of the functions ascribed to IMD 916 or a processor thereof may be performed by one or more other devices, such as programmer 294 or a workstation (not shown), or a processor thereof. For example, programmer 924 may process EGM signals received from IMD 916 and/or cardiac mechanical contraction information to according to the techniques described herein. Furthermore, although described herein with respect to an IMD, in other examples, the techniques described herein may be performed by or implemented in an external medical device, which may be coupled to a patient via percutaneous or transcutaneous leads.

Figure 11C:
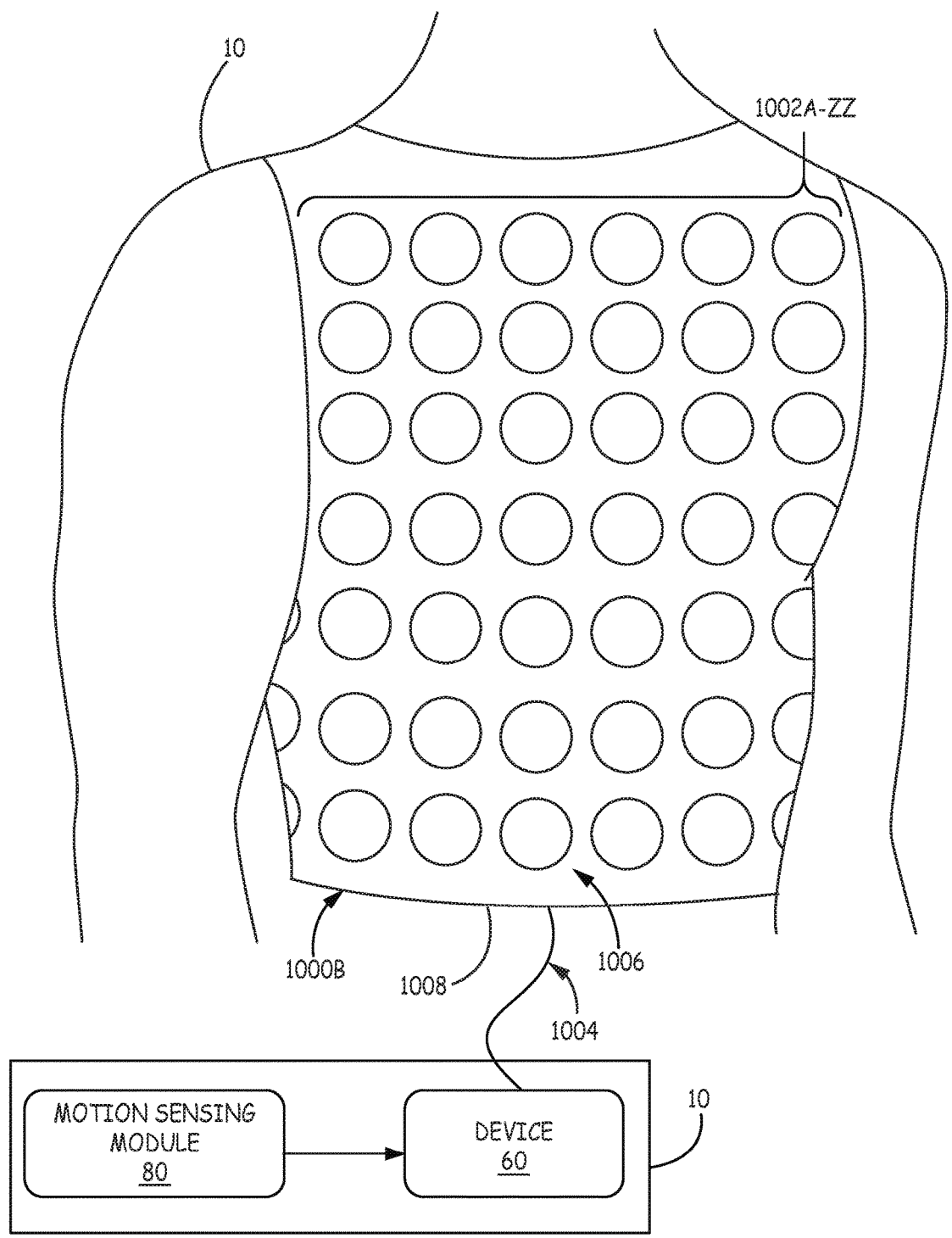

FIGS. 11B and 11C are conceptual diagrams illustrating example systems for measuring body-surface potentials and, more particularly, torso-surface potentials. In one example illustrated in FIG. 11B, sensing device 1000A, comprising a set of electrodes 1002A-F (generically "electrodes 1002") and strap 1008, is wrapped around the torso of patient 914 such that the electrodes surround heart 912. As illustrated in FIG. 11B, electrodes 1002 may be positioned around the circumference of patient 914, including the posterior, lateral, and anterior surfaces of the torso of patient 914. In other examples, electrodes 1002 may be positioned on any one or more of the posterior, lateral, and anterior surfaces of the torso. Electrodes 1002 may be electrically connected to a processing unit such as device 60 via wired connection 1004. Some configurations may use a wireless connection to transmit the signals sensed by electrodes 1002 to device 60, e.g., as channels of data.

Although in the example of FIG. 11B sensing device 1000A comprises strap 1008, in other examples any of a variety of mechanisms, e.g., tape or adhesives, may be employed to aid in the spacing and placement of electrodes 1002. In some examples, strap 1008 may comprise an elastic band, strip of tape, or cloth. In some examples, electrodes 1002 may be placed individually on the torso of patient 914.

Electrodes 1002 may surround heart 912 of patient 914 and record the electrical signals associated with the depolarization and repolarization of heart 912 after the signals have propagated through the torso of patient 914. Each of electrodes 1002 may be used in a unipolar configuration to sense the torso-surface potentials that reflect the cardiac signals. Device 60 may also be coupled to a return or indifferent electrode (not shown) which may be used in combination with each of electrodes 1002 for unipolar sensing. In some examples, there may be 12 to 16 electrodes 1002 spatially distributed around the torso of patient 914. Other configurations may have more or fewer electrodes 1002.

Processing unit 60 may record and analyze the torso-surface potential signals sensed by electrodes 1002. As described herein, device 60 may be configured to provide an output to a user. The user may make a diagnosis, prescribe CRT, position therapy devices, e.g., leads, or adjust or select treatment parameters based on the indicated output.

In some examples, the analysis of the torso-surface potential signals by device 60 may take into consideration the location of electrodes 1002 on the surface of the torso of patient 914. In such examples, device 60 may be communicatively coupled to an motion sensing module 80 such as a programmer, which may provide an image that allows device 60 to determine coordinate locations of each of electrodes 1002 on the surface of patient 914. Electrodes 1002 may be visible, or made transparent through the inclusion or removal of certain materials or elements, in the image provided by motion sensing module 80.

FIG. 11C illustrates an example configuration of a system that may be used to evaluate cardiac response in heart 912 of patient 914. The system comprises a sensing device 1000B, which may comprise vest 1006 and electrodes 1002 A-ZZ (generically "electrodes 1002"), a device 60, and imaging system 501. Device 60 and imaging system 501 may perform substantially as described above with respect to FIG. 11A. As illustrated in FIG. 11C, electrodes 1002 are distributed over the torso of patient 914, including the anterior, lateral, and posterior surfaces of the torso of patient 914.

Sensing device 1000B may comprise a fabric vest 1006 with electrodes 1002 attached to the fabric. Sensing device 1000B may maintain the position and spacing of electrodes 1002 on the torso of patient 914. Sensing device 1000B may be marked to assist in determining the location of electrodes 1002 on the surface of the torso of patient 914. In some examples, there may be 150 to 256 electrodes 1002 distributed around the torso of patient 914 using sensing device 1000B, though other configurations may have more or fewer electrodes 1002.

The ECG data is mapped to a generic, graphical model of a patient's torso and/or heart and a graphical display is produced on a graphical user interface without taking an actual image, such as an MRI or CT image, from the patient. The resolution of the ECG data mapped to a graphical anatomical model depends on the number and spacing of surface electrodes 1002 used. In some examples, there may be 12 to 16 electrodes spatially distributed around the torso of patient 914. Other configurations may have more or fewer electrodes. In one embodiment, a minimum number of electrodes includes twelve electrodes arranged in two rows extending along the posterior torso and twelve electrodes arranged in two rows extending along the anterior torso for a total of twenty-four electrodes, which may be equally distributed circumferentially around the torso.

FIG. 12 is a conceptual diagram illustrating IMD 916 and leads 918, 920, and 922 of system 910 in greater detail. In the illustrated example, bipolar electrodes 940 and 942 are located adjacent to a distal end of lead 918. In addition, bipolar electrodes 944 and 946 are located adjacent to a distal end of lead 920, and bipolar electrodes 948 and 950 are located adjacent to a distal end of lead 922.

In the illustrated example, electrodes 940, 944 and 948 take the form of ring electrodes, and electrodes 942, 946 and 950 may take the form of extendable helix tip electrodes mounted retractably within insulative electrode heads 952, 954 and 956, respectively. Leads 918, 920, 922 also include elongated electrodes 962, 964, 966, respectively, which may take the form of a coil. In some examples, each of the electrodes 940, 942, 944, 946, 948, 950, 962, 964 and 966 is electrically coupled to a respective conductor within the lead body of its associated lead 918, 920, 922, and thereby coupled circuitry within IMD 916.

In some examples, IMD 916 includes one or more housing electrodes, such as housing electrode 904 illustrated in FIG. 12, which may be formed integrally with an outer surface of hermetically-sealed housing 908 of IMD 916 or otherwise coupled to housing 908. In some examples, housing electrode 904 is defined by an uninsulated portion of an outward facing portion of housing 908 of IMD 916. Other division between insulated and uninsulated portions of housing 908 may be employed to define two or more housing electrodes. In some examples, a housing electrode comprises substantially all of housing 908.

As described in further detail with reference to FIG. 13, housing 908 encloses a signal generator that generates therapeutic stimulation, such as cardiac pacing, cardioversion and defibrillation pulses, as well as a sensing module for sensing electrical signals attendant to the depolarization and repolarization of heart 912. Housing 908 may also enclose a wave detection module that detects the onsets and offsets of heart depolarization and repolarization waves. The wave detection module may be enclosed within housing 908. Alternatively, the wave detection module may housed in a remote piece of equipment, such as programmer 924 or a workstation (not shown) and communicate with the IMD 916 through wireless communication.

IMD 916 senses electrical signals attendant to the depolarization and repolarization of heart 912 via electrodes 904, 940, 942, 944, 946, 948, 950, 962, 964 and 966. IMD 916 may sense such electrical signals via any bipolar combination of electrodes 940, 942, 944, 946, 948, 950, 962, 964 and 966. Furthermore, any of the electrodes 940, 942, 944, 946, 948, 950, 962, 964 and 966 may be used for unipolar sensing in combination with housing electrode 904.

In some examples, IMD 916 delivers pacing pulses via bipolar combinations of electrodes 940, 942, 944, 946, 948 and 950 to produce depolarization of cardiac tissue of heart 912. In some examples, IMD 16 delivers pacing pulses via any of electrodes 940, 942, 944, 946, 948 and 950 in combination with housing electrode 904 in a unipolar configuration. Furthermore, IMD 916 may deliver cardioversion or defibrillation pulses to heart 12 via any combination of elongated electrodes 962, 964, 966, and housing electrode 904.

The illustrated numbers and configurations of leads 918, 920, and 922 and electrodes are merely examples. Other configurations, i.e., number and position of leads and electrodes, are possible. In some examples, system 910 may include an additional lead or lead segment having one or more electrodes positioned at different locations in the cardiovascular system for sensing and/or delivering therapy to patient 914. For example, instead of or in addition to intracardiac leads 918, 920 and 922, system 910 may include one or more epicardial or subcutaneous leads not positioned within the heart. In some examples, the subcutaneous leads may sense a subcutaneous cardiac electrogram, for example the far-field electrogram between the SVC coil and the can. The subcutaneous cardiac electrogram may substitute for the surface ECG in determining the global electromechanical delay.

FIG. 13 is a block diagram illustrating an example configuration of IMD 916. In the illustrated example, IMD 916 includes a processor 970, memory 972, signal generator 974, sensing module 976, telemetry module 978, motion sensing module 980, wave detection module 982 and peak detection module 984. Memory 972 includes computer-readable instructions that, when executed by processor 970, causes IMD 916 and processor 970 to perform various functions attributed to IMD 916 and processor 970 herein. Memory 972 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media.

Processor 970 may include any one or more of a microprocessor, a controller, a digital signal processor (DSP), an application specific integrated circuit (ASIC), a field-programmable gate array (FPGA), or equivalent discrete or analog logic circuitry. In some examples, processor 970 may include multiple components, such as any combination of one or more microprocessors, one or more controllers, one or more DSPs, one or more ASICs, or one or more FPGAs, as well as other discrete or integrated logic circuitry. The functions attributed to processor 970 herein may be embodied as software, firmware, hardware or any combination thereof. Generally, processor 970 controls signal generator 974 to deliver stimulation therapy to heart 912 of patient 914 according to a selected one or more of therapy programs or parameters, which may be stored in memory 972. As an example, processor 970 may control signal generator 974 to deliver electrical pulses with the amplitudes, pulse widths, frequency, or electrode polarities specified by the selected one or more therapy programs.

Signal generator 974 is configured to generate and deliver electrical stimulation therapy to patient 912. As shown in FIG. 13, signal generator 974 is electrically coupled to electrodes 94, 940, 942, 944, 946, 948, 950, 962, 964, and 966, e.g., via conductors of the respective leads 918, 920, and 922 and, in the case of housing electrode 904, within housing 908. For example, signal generator 974 may deliver pacing, defibrillation or cardioversion pulses to heart 912 via at least two of electrodes 94, 940, 942, 944, 946, 948, 950, 962, 964, and 966. In other examples, signal generator 974 delivers stimulation in the form of signals other than pulses, such as sine waves, square waves, or other substantially continuous time signals.

Signal generator 974 may include a switch module (not shown) and processor 970 may use the switch module to select, e.g., via a data/address bus, which of the available electrodes are used to deliver the electrical stimulation. The switch module may include a switch array, switch matrix, multiplexer, or any other type of switching device suitable to selectively couple stimulation energy to selected electrodes. Electrical sensing module 976 monitors electrical cardiac signals from any combination of electrodes 904, 940, 942, 944, 946, 948, 950, 962, 964, and 966. Sensing module 976 may also include a switch module which processor 970 controls to select which of the available electrodes are used to sense the heart activity, depending upon which electrode combination is used in the current sensing configuration.

Sensing module 976 may include one or more detection channels, each of which may comprise an amplifier. The detection channels may be used to sense the cardiac signals. Some detection channels may detect events, such as R-waves or P-waves, and provide indications, such as wave markers, of the occurrences of such events to processor 970. One or more other detection channels may provide the signals to an analog-to-digital converter, for conversion into a digital signal for processing or analysis by processor 970.

For example, sensing module 976 may comprise one or more narrow band channels, each of which may include a narrow band filtered sense-amplifier that compares the detected signal to a threshold. If the filtered and amplified signal is greater than the threshold, the narrow band channel indicates that a certain electrical cardiac event, e.g., depolarization, has occurred. Processor 970 then uses that detection in measuring frequencies of the sensed events.

In one example, at least one narrow band channel may include an R-wave or P-wave amplifier. In some examples, the R-wave and P-wave amplifiers may take the form of an automatic gain controlled amplifier that provides an adjustable sensing threshold as a function of the measured R-wave or P-wave amplitude. Examples of R-wave and P-wave amplifiers are described in U.S. Pat. No. 5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety.

In some examples, sensing module 976 includes a wide band channel which may comprise an amplifier with a relatively wider pass band than the narrow band channels. Signals from the electrodes that are selected for coupling to this wide-band amplifier may be converted to multi-bit digital signals by an analog-to-digital converter (ADC) provided by, for example, sensing module 976 or processor 970. Processor 970 may analyze the digitized versions of signals from the wide band channel. Processor 970 may employ digital signal analysis techniques to characterize the digitized signals from the wide band channel to, for example, detect and classify the patient's heart rhythm.

Processor 970 may detect and classify the patient's heart rhythm based on the cardiac electrical signals sensed by sensing module 976 employing any of the numerous signal processing methodologies known in the art. For example, processor 970 may maintain escape interval counters that may be reset upon sensing of R-waves by sensing module 976. The value of the count present in the escape interval counters when reset by sensed depolarizations may be used by processor 970 to measure the durations of R-R intervals, which are measurements that may be stored in memory 972. Processor 970 may use the count in the interval counters to detect a tachyarrhythmia, such as ventricular fibrillation or ventricular tachycardia. A portion of memory 972 may be configured as a plurality of recirculating buffers, capable of holding series of measured intervals, which may be analyzed by processor 970 to determine whether the patient's heart 912 is presently exhibiting atrial or ventricular tachyarrhythmia.

In some examples, processor 970 may determine that tachyarrhythmia has occurred by identification of shortened R-R interval lengths. Generally, processor 970 detects tachycardia when the interval length falls below 360 milliseconds (ms) and fibrillation when the interval length falls below 320 ms. These interval lengths are merely examples, and a user may define the interval lengths as desired, which may then be stored within memory 972. This interval length may need to be detected for a certain number of consecutive cycles, for a certain percentage of cycles within a running window, or a running average for a certain number of cardiac cycles, as examples.

In some examples, an arrhythmia detection method may include any suitable tachyarrhythmia detection algorithms. In one example, processor 970 may utilize all or a subset of the rule-based detection methods described in U.S. Pat. No. 5,545,186 to Olson et al., entitled, "PRIORITIZED RULE BASED METHOD AND APPARATUS FOR DIAGNOSIS AND TREATMENT OF ARRHYTHMIAS," which issued on Aug. 13, 1996, or in U.S. Pat. No. 5,755,736 to Gillberg et al., entitled, "PRIORITIZED RULE BASED METHOD AND APPARATUS FOR DIAGNOSIS AND TREATMENT OF ARRHYTHMIAS," which issued on May 26, 1998. U.S. Pat. No. 5,545,186 to Olson et al. U.S. Pat. No. 5,755,736 to Gillberg et al. is incorporated herein by reference in their entireties. However, other arrhythmia detection methodologies may also be employed by processor 970 in other examples. For example, EGM morphology may be considered in addition to or instead of interval length for detecting tachyarrhythmias.

Generally, processor 970 detects a treatable tachyarrhythmia, such as VF, based on the EGM, e.g., the R-R intervals and/or morphology of the EGM, and selects a therapy to deliver to terminate the tachyarrhythmia, such as a defibrillation pulse of a specified magnitude. The detection of the tachyarrhythmia may include a number of phases or steps prior to delivery of the therapy, such as first phase, sometimes referred to as detection, in which a number of consecutive or proximate R-R intervals satisfies a first number of intervals to detect (NID) criterion, a second phase, sometimes referred to as confirmation, in which a number of consecutive or proximate R-R intervals satisfies a second, more restrictive NID criterion. Tachyarrhythmia detection may also include confirmation based on EGM morphology or other sensors subsequent to or during the second phase.

In the illustrated example, IMD 916 also includes peak detection module 980, wave detection module 982, and motion sensing module 984. Peak detection module 980 and wave detection module 982 may be configured and provide the functionality ascribed to peak detection module 76 and wave detection module 78 herein. Peak detection module 980 may be configured to determine a maximum value of a particular signal. For example, peak detection module 980 may be configured to receive an electrical signal from wave detection module 982 or processor 970 and determine a maximum value of the received signal. Peak detection module 980 may, in some examples, comprise a narrow-band channel of sensing module 976 that is configured to detect R-waves, P-waves, or T-waves in cardiac electrogram signals, e.g., using an amplifier with automatically adjusting threshold.

Generally, wave detection module 982 determines the onsets and offsets on the heart depolarization and repolarizations waves. Wave detection module 982 may be similar to the wave detection module described previously, e.g. wave detection module 78, and more accurately described in FIG. 2. For example, wave detection module may include a low-pass filter, a window module, a slope module, a rectifier module, a smoothing module, and a threshold detection module. Wave detection module 982 may perform substantially similar to the wave detection module described previously in this application.

Peak detection module 980 and wave detection module 982 may receive a cardiac electrogram from sensing module 976, e.g., from a wide-band channel of the sensing module. In some examples, the cardiac electrogram may be a far-field cardiac electrogram, e.g., between superior vena cava coil 766 and housing electrode 904. A far-field cardiac electrogram may be used in the manner described herein with respect to a surface ECG, e.g., to determine a global electromechanical delay. In some examples, the cardiac electrogram may be a unipolar cardiac electrogram between housing electrode 906 and any of electrodes 942, 944, 946 and 950. The unipolar cardiac electrogram may be received from sensing module 976, e.g., via a wide-band channel of the sensing module, and may be used in the manner described herein with respect to local cardiac electrogram signals, e.g., to determine local electromechanical delays.

Motion sensing module 984 may sense the mechanical contraction of the heart, e.g., at one or more cardiac sites. Motion sensing module 984 may be electrically coupled to one or more sensors that generate a signal that varies based on cardiac contraction or motion generally, such as one or more accelerometers, pressure sensors, impedance sensors, or flow sensors. The detected contraction may be contraction of cardiac tissue at a particular location, e.g., a particular portion of a ventricular wall.

Although processor 970 and wave detection module 982 are illustrated as separate modules in FIG. 13, processor 970 and wave detection module 982 may be incorporated in a single processing unit. Wave detection module 982, and any of its components, may be a component of or module executed by processor 970.

Telemetry module 978 includes any suitable hardware, firmware, software or any combination thereof for communicating with another device, such as programmer 924 (FIG. 11). In some examples, programmer 924 may include a programming head that is placed proximate to the patient's body near the IMD 916 implant site, and in other examples programmer 924 and IMD 916 may be configured to communicate using a distance telemetry algorithm and circuitry that does not require the use of a programming head and does not require user intervention to maintain a communication link. Under the control of processor 970, telemetry module 978 may receive downlink telemetry from and send uplink telemetry to programmer 924 with the aid of an antenna, which may be internal and/or external. In some examples, processor 970 may transmit cardiac signals produced by sensing module 976 and/or signals generated by heart sound sensor 982 to programmer 924. Processor 970 may also generate and store marker codes indicative of different cardiac events that sensing module 976 or heart sound analyzer 980 detects, and transmit the marker codes to programmer 924. An example IMD with marker-channel capability is described in U.S. Pat. No. 4,374,382 to Markowitz, entitled, "MARKER CHANNEL TELEMETRY SYSTEM FOR A MEDICAL DEVICE," which issued on Feb. 15, 1983 and is incorporated herein by reference in its entirety. Information which processor 970 may transmit to programmer 924 via telemetry module 978 may also include indications of treatable rhythms, and indications of non-treatable rhythms in which the EGM based indication indicated that the rhythm was treatable and the heart sound based indication indicated that the rhythm was non-treatable. Such information may be included as part of a marker channel with an EGM.

The flow diagram depicted in FIG. 15 discloses a computer-implemented method 1100 that determines onsets and/or offsets of cardiac depolarization waves without using a threshold-based detection algorithm. Detection of onset of a depolarization wave is desirable since CRT may be optimized. By way of illustration, CRT data such as q-LV times and activation times are automatically determined, which is useful when implanting a left ventricular lead. For example, a programmer can be set to automatically check if the local q-LV time is greater than a predetermined value (e.g. 90-100 ms). If the local q-LV time is greater than the predetermined value, the local q-LV time is displayed on the graphical user interface of the programmer to the user (e.g. physician or implanter) so that the left ventricular lead can be properly positioned. Generally, sites with q-LV>90-100 ms sites are preferable for LV lead implantation as opposed to sites with a shorter q-LV.

Implementation of method 1100 requires a plurality of body-surface electrodes such as an ECG belt or vest be placed around the torso of the patient. An exemplary ECG belt or vest is described in U.S. patent application Ser. No.

13/462,404, filed May 2, 2012, entitled "Assessing Intra-Cardiac Activation Patterns And Electrical Dyssynchrony" and assigned to the assignee of the present invention, the disclosure of which is incorporated by reference in its entirety herein. After the vest or belt is secured around the patient's torso, the programmer is activated. Exemplary programmers that can be used to acquire signals from implanted and surface electrodes includes the Medtronic Carelink Programmer Model 2090 and the Model 2290 Analyzer or the CARELINK ENCORE™. Medtronic Vitatron Reference Manual CARELINK ENCORE™ (2013) available at http://manuals.medtronic.com/manuals/main/as/en/manual, the disclosure of which is incorporated by reference in its entirety.

Far-field EGMs, ECG, or ECG-like signals are acquired from an electrode that is the greatest distance away from the pacing electrode. If an IMD is implanted, electrodes that can produce far field signals include superior vena cava (SVC) electrode-pulse generator housing (also referred to as a "can"), right ventricle (RV) coil-can etc.).

Method 1100 starts at operation 1102 in which a baseline rhythm is acquired from a plurality of body-surface electrodes and then stored into memory. The baseline rhythm includes fiducials such as an atrial wave marker and a ventricular wave marker. The atrial wave marker is associated with an atrial event (e.g., an atrial sense, etc.), while a ventricular wave marker is associated with a ventricular event (e.g., a ventricular sense, etc.). Each marker can be displayed to a user on a graphical user interface of a computer such as a programmer.

At block 1104, a pre-specified window is set. The pre-specified window can be defined as extending from the atrial marker to the ventricular marker, an example of which is shown along the ECG signal in FIG. 16A. The y-axis is in millivolts (mv) and the x-axis is time in milliseconds (ms) for FIG. 16A.

A low pass filter is then applied at block 1106 to the ECG signal within the pre-specified window. The low-pass filter can be a Bessel filter with a cut-off frequency of 15 Hz, 20 Hz or a frequency value between 15 Hz and 20 Hz. The signal(s) acquired from the plurality of surface electrodes and/or the electrodes associated with the implantable medical device is passed through the low pass filter, which causes the removal of any spurious high-frequency artifacts or components from the far-field ECG-like signal.

Figure 16B:
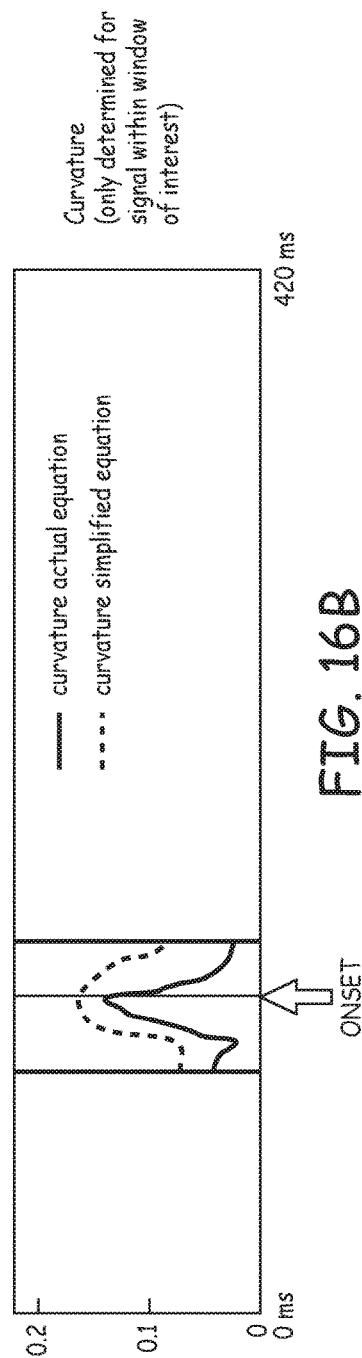
FIG. 16B graphically depicts a curvature relative to the cardiac ECG signal shown in FIG. 16A.

A rectified slope of the signal within the window is determined at block 1108 using module 96 depicted in FIG. 2. Rectification of a signal can be performed by any known method. At block 1110, a time point (t1) (shown in FIG. 16A) is determined such that the rectified slope exceeds 10% of a maximum value of the rectified slope. A point of onset of a depolarization complex in the signal is determined at block 1112. The point of onset of the depolarization signal requires the radii of the curvature of the signal within the pre-specified window to be determined, as shown in FIG. 16B. The radii is plotted along a y-axis in curvature (curvature-mV) units and a x-axis in time of milliseconds. The radius of the curvature equation used to plot FIG. 16B is defined as $r=|y''|/(1+|y'|^2)^{(3/2)}$ in which $y''$ and $y'$ are the double and single derivatives of respectively. y is the signal acquired from surface electrodes and/or electrodes associated with an implanted medical device. The first and second derivatives of the signal, represented by $y=f(t)$, can be determined using a variety of known methods. Firmware or other computer instructions, stored in memory, can determine the derivatives of $y(t)$. For example, the first derivative, $y'$, can be determined by repeatedly calculating the slope between two different points along the signal. The second derivative, $y''$ can be similarly calculated but instead of using $y(t)$, different points along $y'$ curve are used. In another embodiment an algorithm a simplified expression tracking the curvature may be used like $r \approx |y'''|/(1+|y'|^2)$ which makes it easier from the computational standpoint, eliminating the need of computing square roots. The simplified curvature equation $r \approx |y''|/(1+|y'|2)$, (the radii shown by the dashed line in FIG. 16B), can also be used to compute an index that tracks the curvature.

In particular, the algorithm searches radii along points in the curve in order to locate the greatest curvature (shown in FIGS. 16A-16B) within a window of pre-specified width and ending on the maximum peak, or minimum valley. The radius of the curvature is solely determined for the signal within the pre-specified window. In one or more other embodiments involving biphasic signals, the algorithm is configured to search for the greatest curvature within a window of pre-specified width and ending on the maximum peak, or minimum valley, whichever is greater in magnitude between the maximum and minimum peaks.

The onset of depolarization is identified by the point associated with the maximum curvature within the search window, as shown in FIGS. 16A-16B. In particular, the point of onset occurs at a largest curvature in the signal within the window from Vs-100 ms to t1. The largest curvature in the signal occurs at the highest value at points in which a sharp deflection exists which is indicative of the onset of depolarization on an ECG-like signal. After determining the onset of depolarization, the user can make appropriate adjustments to the implantable medical device in order to optimize CRT. While the techniques described in FIG. 15 have been applied to the onset of depolarization, the same principles can be applied to detection of the onset of repolarization signals such as T waves. As applied to repolarization signals, useful data can be obtained for adjusting Q-T intervals for CRT.

The stable and reliable algorithm, described in method 1100, detects QRS onset with minimum inputs or manipulation from the user. Additionally, the algorithm may be incorporated within an IMD (e.g. CRT device) for marking the onset of QRS waves on leadless ECG or ECG or other far-field ECG-like signals. By incorporating the algorithm into the IMD, measurements of electrical activation times are automated with respect to the onset of QRS waves and/or T waves.

The techniques described in this disclosure, including those attributed to IMD wave detection module 80, programmer 24, or various constituent components, may be implemented, at least in part, in hardware, software, firmware or any combination thereof. For example, various aspects of the techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

There are a variety of other embodiments that can be employed for the pre-specified window used in FIG. 15. For example, the pre-specified window can be set to begin at an atrial wave marker and extend a certain length of time or to another marker. In yet another embodiment, the pre-specified window can be set to begin at a ventricular wave marker and extend a certain length of time or to another marker.

When implemented in software, the functionality ascribed to the systems, devices and techniques described in this disclosure may be embodied as instructions on a computer-readable medium such as random access memory (RAM), read-only memory (ROM), non-volatile random access memory (NVRAM), electrically erasable programmable read-only memory (EEPROM), FLASH memory, magnetic data storage media, optical data storage media, or the like. The instructions may be executed to support one or more aspects of the functionality described in this disclosure.

The invention claimed is:

1. A method of selecting an implant site for an implantable pacing electrode, the method comprising:
    sensing an intrinsic heart rhythm signal using a plurality of body-surface electrodes, wherein the intrinsic heart rhythm signal includes an atrial marker and a ventricular marker;
    sensing a cardiac contraction signal comprising heart mechanical contraction information, wherein the heart mechanical contraction information comprises times of local cardiac contraction;
    determining a global electromechanical delay for each of a plurality of candidate cardiac pacing sites, wherein determining each global electromechanical delay comprises:
        defining a window between the atrial marker and the ventricular marker of the intrinsic heart rhythm signal sensed using the plurality of body-surface electrodes,
        determining a point of onset of a depolarization complex in the intrinsic heart rhythm signal within the defined window,
        sensing a time of local cardiac contraction within a window of the cardiac contraction signal corresponding to the defined window; and
        determining the global electromechanical delay for the candidate cardiac pacing site between the determined point of onset of the depolarization complex within the defined window and the time of local cardiac contraction within the corresponding window;
    selecting two or more of the plurality of candidate cardiac pacing sites as potential implant sites for an implantable pacing electrode for delivering cardiac pacing based upon the determined global electromechanical delays;
    sensing a local intrinsic heart rhythm signal using one or more electrodes at localized heart tissue, wherein the local intrinsic heart rhythm signal includes a local atrial marker and a local ventricular marker;
    sensing a local cardiac contraction signal comprising heart mechanical contraction information, wherein the heart mechanical contraction information comprises times of local cardiac contraction;
    determining a local electromechanical delay for each of the selected two or more of the plurality of candidate cardiac pacing sites, wherein determining each local electromechanical delay comprises:
        defining a local window between the local atrial marker and the local ventricular marker of the local intrinsic heart rhythm signal sensed using the one or more electrodes at localized heart tissue,
        determining a point of onset of a local depolarization complex in the local intrinsic heart rhythm signal,
        sensing a time of local cardiac contraction within a window of the local cardiac contraction signal corresponding to the defined local window; and
        determining the local electromechanical delay for the selected candidate cardiac pacing site between the determined point of onset of the local depolarization complex within the defined local window and the time of local cardiac contraction within the corresponding window; and
    identifying a subset of the selected two or more of the plurality of candidate cardiac pacing sites as potential pacing sites to be paced by an implantable electrode based on the local electromechanical delays.

2. The method of claim 1, wherein determining the global electromechanical delay from the intrinsic heart rhythm for each of a plurality of candidate cardiac pacing sites further comprises:
    applying a low pass filter to the intrinsic heart rhythm signal within the defined window,
    determining a rectified slope of the intrinsic heart rhythm signal, and
    determining a time point (t1) in which the rectified slope exceeds a defined percentage of a maximum value of the rectified slope, wherein the point of onset occurs at a largest curvature in the intrinsic heart rhythm signal within the defined window prior to t1.

3. The method of claim 2, wherein the largest curvature in the signal is determined from a curvature of the signal defined as:
    $r=|y''|/(1+|y'|^2)^{(3/2)}$ in which y'' and y' are the double and single derivatives of y=f(t), respectively.

4. The method of claim 2, wherein $r \approx |y''|/(1+|y'|2)$ is used to compute an index that tracks the curvature of the signal.

5. The method of claim 1, wherein determining the point of onset of the local depolarization complex comprises searching the signal, or in an index tracking a curvature of the signal, for a sharp deflection in the curvature of the signal relative to other portions of the signal, the sharp deflection being indicative of the onset of the local depolarization complex.

6. The method of claim 1, wherein sensing the local intrinsic heart rhythm using one or more electrodes at localized heart tissue comprises receiving a signal by a cardiac resynchronization therapy (CRT) device, wherein determining the point of onset of the local depolarization complex comprises determining a point of onset of a QRS complex in the signal received by the CRT device.

7. The method of claim 1, wherein determining the local electromechanical delay for each of the selected two or more of the plurality of candidate cardiac pacing sites further comprises:
    applying a low pass filter to the intrinsic heart rhythm signal within the defined local window, determining a rectified slope of the intrinsic heart rhythm signal, and determining a time point (t1) in which the rectified slope exceeds a defined percentage of a maximum value of the rectified slope, wherein the point of onset of the local depolarization complex occurs at a largest curvature in the intrinsic heart rhythm signal within the defined local window prior to t1.

8. The method of claim 1, wherein selecting the two or more of the plurality of candidate cardiac pacing sites as potential implant sites for an implantable pacing electrode for delivering cardiac pacing based upon the determined global electromechanical delays comprises selecting two or more of the plurality of candidate cardiac pacing sites as potential implant sites for an implantable pacing electrode for delivering cardiac pacing based on the determined global electromechanical delays being greater than a pre-determined threshold.

9. The method of claim 1, wherein identifying the subset of the selected two or more of the plurality of candidate cardiac pacing sites as potential implant sites for an implantable pacing electrode for delivering cardiac pacing comprises identifying the subset of the selected two or more of the plurality of candidate cardiac pacing sites based on the determined local electromechanical delays being less than a pre-determined threshold.

10. A method of selecting an implant site for an implantable pacing electrode, the method comprising:
sensing an intrinsic heart rhythm signal using a plurality of body-surface electrodes, wherein the intrinsic heart rhythm signal includes an atrial marker and a ventricular marker;
sensing a cardiac contraction signal comprising heart mechanical contraction information, wherein the heart mechanical contraction information comprises times of local cardiac contraction;
determining a global electromechanical delay for each of a plurality of candidate cardiac pacing sites, wherein each global electromechanical delay is determined between a determined point of onset of a depolarization complex of the intrinsic heart rhythm signal sensed using the plurality of body-surface electrodes and a time of local cardiac contraction;
selecting two or more of the plurality of candidate cardiac pacing sites as potential implant sites for an implantable pacing electrode for delivering cardiac pacing based upon the determined global electromechanical delays;
sensing an local intrinsic heart rhythm signal using one or more electrodes at localized heart tissue, wherein the local intrinsic heart rhythm signal includes a local atrial marker and a local ventricular marker;
sensing a local cardiac contraction signal comprising heart mechanical contraction information, wherein the heart mechanical contraction information comprises times of local cardiac contraction;
determining a local electromechanical delay for each of the selected two or more of the plurality of candidate cardiac pacing sites, wherein each local electromechanical delay is determined between a determined point of onset of a local depolarization complex of the local intrinsic heart rhythm signal sensed using the one or more electrodes at localized heart tissue and a time of local cardiac contraction; and
identifying a subset of the selected two or more of the plurality of candidate cardiac pacing sites as potential pacing sites to be paced by an implantable electrode based on the local electromechanical delays.

11. The method of claim 10, wherein each global electromechanical delay is determined between the determined point of onset of the depolarization complex within a defined window between the atrial marker and the ventricular marker of the intrinsic heart rhythm signal sensed using the plurality of body-surface electrodes and the time of local cardiac contraction in a window of the cardiac contraction signal corresponding to the defined window.

12. The method of claim 10, wherein each local electromechanical delay is determined between the determined point of onset of the local depolarization complex within a defined window between the atrial marker and the ventricular marker of the local intrinsic heart rhythm signal sensed using the one or more electrodes at localized heart tissue and the time of local cardiac contraction in a window of the local cardiac contraction signal corresponding to the defined window.

13. The method of claim 10, wherein determining the global electromechanical delay from the intrinsic heart rhythm signal for each of a plurality of candidate cardiac pacing sites further comprises:
applying a low pass filter to the intrinsic heart rhythm signal within a defined window,
determining a rectified slope of the intrinsic heart rhythm signal, and
determining a time point (t1) in which the rectified slope exceeds a defined percentage of a maximum value of the rectified slope, wherein the point of onset occurs at a largest curvature in the intrinsic heart rhythm signal within the defined window prior to t1.

14. The method of claim 10, wherein determining the local electromechanical delay for each of the selected two or more of the plurality of candidate cardiac pacing sites further comprises:
applying a low pass filter to the local intrinsic heart rhythm signal within a local defined window,
determining a rectified slope of the local intrinsic heart rhythm signal, and
determining a time point (t1) in which the rectified slope exceeds a defined percentage of a maximum value of the rectified slope, wherein the point of onset occurs at a largest curvature in the local intrinsic heart rhythm signal within the defined window prior to t1.

15. A method of selecting an implant site for an implantable pacing electrode, the method comprising:
delivering a pace at a localized region of a heart;
sensing a heart rhythm signal using one or more body-surface electrodes, wherein the heart rhythm signal includes an atrial marker and a ventricular marker;
determining an electromechanical delay from the heart rhythm signal for the delivered pace, the electromechanical delay being between a time of the delivery of the pace and a point of onset of a depolarization complex of the heart rhythm signal, wherein determining the point of onset of a depolarization complex of the heart rhythm signal comprises:
defining a window between the atrial marker and the ventricular marker,
applying a low pass filter to the heart rhythm signal within the defined window,
determining a rectified slope of the heart rhythm signal,
determining a time point (t1) in which the rectified slope exceeds a defined percentage of a maximum value of the rectified slope, determining the point of onset of the depolarization complex of the heart rhythm signal at a largest curvature in the heart rhythm signal within the defined window prior to t1, and determining whether the electromechanical delay exceeds a threshold; and indicating that the localized region of the heart paced is not suitable for implantation of an implantable electrode when the electromechanical delay exceeds the threshold.

16. The method of claim 15, wherein the largest curvature in the heart rhythm signal is determined from a curvature of the signal defined as:

$r=|y''|/(1+|y'|^2)^{(3/2)}$ in which y'' and y' are the double and single derivatives of y=f(t), respectively.

17. The method of claim 15, wherein $r \approx |y''|/(1+|y'|2)$ is used to compute an index that tracks the curvature of the heart rhythm signal.

18. The method of claim 15, wherein determining the point of onset of the depolarization complex comprises searching the heart rhythm signal, or in an index tracking a curvature of the heart rhythm signal, for a sharp deflection in the curvature of the heart rhythm signal relative to other portions of the signal, the sharp deflection being indicative of the onset of the depolarization complex.

* * * * *